(12) United States Patent
Hall et al.

(10) Patent No.: US 10,953,586 B2
(45) Date of Patent: *Mar. 23, 2021

(54) METHODS, SYSTEMS, AND APPARATUSES FOR MANUFACTURING ROTATIONAL SPUN APPLIANCES

(71) Applicant: Merit Medical Systems, Inc., South Jordan, UT (US)

(72) Inventors: John William Hall, North Salt Lake, UT (US); Randal Boyd, Riverton, UT (US); Dylan Neyme, Salt Lake City, UT (US); F. Mark Ferguson, Salt Lake City, UT (US)

(73) Assignee: Merit Medical Systems, Inc., South Jordan, UT (US)

(*) Notice: Subject to any disclaimer, the term of this patent is extended or adjusted under 35 U.S.C. 154(b) by 199 days.

This patent is subject to a terminal disclaimer.

(21) Appl. No.: 15/806,020

(22) Filed: Nov. 7, 2017

(65) Prior Publication Data

US 2018/0056568 A1 Mar. 1, 2018

Related U.S. Application Data

(62) Division of application No. 14/204,466, filed on Mar. 11, 2014, now Pat. No. 9,827,703.

(Continued)

(51) Int. Cl.
*B29C 48/05* (2019.01)
*D01D 5/18* (2006.01)

(Continued)

(52) U.S. Cl.
CPC ............. *B29C 48/05* (2019.02); *A61F 2/82* (2013.01); *A61F 2/86* (2013.01); *B29C 48/155* (2019.02);

(Continued)

(58) Field of Classification Search
CPC .......... D01D 5/0076; D01D 5/18; D01D 7/00; B29C 48/05; B29C 48/155; A61F 2/82; A61F 2/86; A61F 2240/001
See application file for complete search history.

(56) References Cited

U.S. PATENT DOCUMENTS 2,772,444 A 12/1956 Burrows et al.
3,047,444 A 7/1962 Harwood
(Continued)

FOREIGN PATENT DOCUMENTS

CN 101584612 11/2009
EP 0457456 11/1991
(Continued)

OTHER PUBLICATIONS

Board Decision on Appeal dated Nov. 23, 2018 for U.S. Appl. No. 14/044,050.
(Continued)

*Primary Examiner* — Xiao S Zhao
*Assistant Examiner* — Joseph S Leyson
(74) *Attorney, Agent, or Firm* — Stoel Rives LLP

(57) ABSTRACT

The present disclosure relates to methods and systems for manufacturing rotational spun materials. The rotational spun materials are medical appliances or other prostheses made of, constructed from, covered or coated with rotational spun materials, such as polytetrafluoroethylene (PTFE).

11 Claims, 10 Drawing Sheets

Related U.S. Application Data

(60) Provisional application No. 61/780,524, filed on Mar. 13, 2013.

(51) Int. Cl.

| | | |
|---|---|---|
| *D01D 7/00* | (2006.01) | |
| *A61F 2/86* | (2013.01) | |
| *B29C 48/155* | (2019.01) | |
| *A61F 2/82* | (2013.01) | |
| *D01D 5/00* | (2006.01) | |

(52) U.S. Cl.
CPC ............... *D01D 5/18* (2013.01); *D01D 7/00* (2013.01); *A61F 2240/001* (2013.01); *D01D 5/0076* (2013.01)

(56) References Cited

U.S. PATENT DOCUMENTS

| | | | |
|---|---|---|---|
| 3,203,365 A | 8/1965 | Bowe et al. | |
| 4,043,331 A | 8/1977 | Martin et al. | |
| 4,044,404 A | 8/1977 | Martin et al. | |
| 4,096,227 A | 6/1978 | Gore | |
| 4,127,706 A | 11/1978 | Martin et al. | |
| 4,223,101 A * | 9/1980 | Fine ................ | D01D 5/0038 264/10 |
| 4,323,525 A | 4/1982 | Bornat | |
| 4,345,414 A | 8/1982 | Bornat et al. | |
| 4,552,707 A | 11/1985 | How | |
| 4,689,186 A | 8/1987 | Bornat | |
| 5,167,890 A | 12/1992 | Sasshofer et al. | |
| 5,236,447 A | 8/1993 | Kubo | |
| 5,328,946 A | 7/1994 | Tuminello et al. | |
| 5,344,297 A | 9/1994 | Hills | |
| 5,509,902 A | 4/1996 | Raulerson | |
| 5,512,051 A | 4/1996 | Wang et al. | |
| 5,552,100 A | 9/1996 | Shannon et al. | |
| 5,562,986 A | 10/1996 | Yamamoto et al. | |
| 5,700,572 A | 12/1997 | Klatt et al. | |
| 5,702,658 A | 12/1997 | Pellegrin et al. | |
| 5,741,333 A | 4/1998 | Frid | |
| 5,810,870 A | 9/1998 | Myers et al. | |
| 5,941,910 A | 8/1999 | Schindler et al. | |
| 6,010,529 A | 1/2000 | Herweck et al. | |
| 6,075,180 A | 6/2000 | Sharber et al. | |
| 6,106,913 A | 8/2000 | Scardino | |
| 6,165,212 A | 12/2000 | Dereume et al. | |
| 6,238,430 B1 | 5/2001 | Klumb | |
| 6,306,424 B1 | 10/2001 | Vyakarnam | |
| 6,383,214 B1 | 5/2002 | Banas et al. | |
| 6,436,135 B1 | 8/2002 | Goldfarb | |
| 6,498,207 B1 | 12/2002 | Hoshikawa et al. | |
| 6,517,571 B1 | 2/2003 | Brauker et al. | |
| 6,679,913 B2 | 1/2004 | Homsy | |
| 6,719,783 B2 | 4/2004 | Lentz et al. | |
| 7,115,220 B2 | 10/2006 | Dubson et al. | |
| 7,118,698 B2 | 10/2006 | Armantrout et al. | |
| 7,244,272 B2 | 7/2007 | Dubson et al. | |
| 7,316,754 B2 | 1/2008 | Ide et al. | |
| 7,413,575 B2 | 8/2008 | Phaneuf et al. | |
| 7,416,559 B2 | 8/2008 | Shalaby | |
| 7,485,141 B2 | 2/2009 | Majercak et al. | |
| 7,498,079 B1 | 3/2009 | Donckers | |
| 7,524,527 B2 | 4/2009 | Stenzel | |
| 7,556,634 B2 | 7/2009 | Lee et al. | |
| 7,582,240 B2 | 9/2009 | Marin et al. | |
| 7,655,175 B2 | 2/2010 | Michael et al. | |
| 7,799,261 B2 | 9/2010 | Orr et al. | |
| 7,857,608 B2 | 12/2010 | Fabbricante et al. | |
| 7,914,568 B2 | 3/2011 | Cully et al. | |
| 7,947,069 B2 | 5/2011 | Sanders | |
| 7,981,353 B2 | 7/2011 | Mitchell et al. | |
| 8,052,744 B2 | 11/2011 | Girton | |
| 8,178,030 B2 | 5/2012 | Anneaux et al. | |
| 8,257,640 B2 | 9/2012 | Anneaux et al. | |
| 8,262,979 B2 | 9/2012 | Anneaux et al. | |
| 8,637,109 B2 | 1/2014 | Grewe et al. | |
| 8,691,543 B2 | 4/2014 | Gaudette et al. | |
| 8,771,582 B2 | 7/2014 | Phaneuf et al. | |
| 9,034,031 B2 | 5/2015 | Anneaux | |
| 9,198,999 B2 | 12/2015 | Hall | |
| 9,655,710 B2 | 5/2017 | Eller | |
| 9,775,933 B2 | 10/2017 | Knisley et al. | |
| 9,856,588 B2 | 1/2018 | Anneaux | |
| 10,010,395 B2 | 7/2018 | Puckett | |
| 10,028,852 B2 | 7/2018 | Hall | |
| 10,154,918 B2 | 12/2018 | Haselby et al. | |
| 10,405,963 B2 | 9/2019 | McAlpine | |
| 10,675,850 B2 * | 6/2020 | Hall .................... | D01F 6/12 |
| 2001/0034549 A1 | 10/2001 | Bartholf et al. | |
| 2001/0049551 A1 | 12/2001 | Tseng et al. | |
| 2002/0077693 A1 | 6/2002 | Barclay | |
| 2002/0082675 A1 | 6/2002 | Myers | |
| 2002/0084178 A1 | 7/2002 | Dubson | |
| 2002/0090725 A1 | 7/2002 | Simpson et al. | |
| 2002/0198588 A1 | 12/2002 | Armstrong et al. | |
| 2003/0040772 A1 | 2/2003 | Hyodoh et al. | |
| 2003/0050711 A1 | 3/2003 | Laurencin | |
| 2003/0074049 A1 | 4/2003 | Hoganson | |
| 2003/0100944 A1 | 5/2003 | Laksin et al. | |
| 2003/0114917 A1 | 6/2003 | Holloway et al. | |
| 2003/0139797 A1 | 7/2003 | Johnson | |
| 2003/0195611 A1 | 10/2003 | Greenhalgh et al. | |
| 2003/0211135 A1 | 11/2003 | Greenhalgh et al. | |
| 2004/0030377 A1 | 2/2004 | Dubson et al. | |
| 2004/0033364 A1 | 2/2004 | Spiridigliozzi et al. | |
| 2004/0038038 A1 | 2/2004 | Yeung | |
| 2004/0051201 A1 | 3/2004 | Greenhalgh et al. | |
| 2004/0054397 A1 | 3/2004 | Smith et al. | |
| 2004/0167606 A1 | 8/2004 | Chouinard | |
| 2004/0219345 A1 | 11/2004 | Armantrout et al. | |
| 2005/0053782 A1 | 3/2005 | Sen et al. | |
| 2005/0137675 A1 | 6/2005 | Dubson et al. | |
| 2005/0187605 A1 | 8/2005 | Greenhalgh et al. | |
| 2005/0244453 A1 | 11/2005 | Stucke et al. | |
| 2005/0244639 A1 | 11/2005 | Marin et al. | |
| 2005/0278018 A1 | 12/2005 | Jensen | |
| 2006/0142852 A1 | 6/2006 | Sowinski et al. | |
| 2006/0200232 A1 | 9/2006 | Phaneuf et al. | |
| 2006/0228435 A1 | 10/2006 | Andrady et al. | |
| 2006/0233990 A1 | 10/2006 | Humphrey et al. | |
| 2007/0023131 A1 | 2/2007 | Farnsworth et al. | |
| 2007/0026036 A1 | 2/2007 | Falotico et al. | |
| 2007/0031607 A1 | 2/2007 | Dubson et al. | |
| 2007/0043428 A1 | 2/2007 | Jennings et al. | |
| 2007/0087027 A1 | 4/2007 | Greenhalgh et al. | |
| 2007/0123973 A1 | 5/2007 | Roth | |
| 2007/0142771 A1 | 6/2007 | Durcan | |
| 2007/0207179 A1 | 9/2007 | Andersen et al. | |
| 2007/0207186 A1 | 9/2007 | Scanlon et al. | |
| 2007/0244569 A1 | 10/2007 | Weber et al. | |
| 2007/0269481 A1 | 11/2007 | Li et al. | |
| 2007/0276477 A1 | 11/2007 | Lee et al. | |
| 2008/0021545 A1 | 1/2008 | Reneker et al. | |
| 2008/0029617 A1 | 2/2008 | Marshall et al. | |
| 2008/0118541 A1 | 5/2008 | Pacetti | |
| 2008/0119943 A1 | 5/2008 | Armstrong et al. | |
| 2008/0199506 A1 | 8/2008 | Horres et al. | |
| 2008/0208323 A1 | 8/2008 | El-Kurdi et al. | |
| 2008/0208325 A1 | 8/2008 | Helmus et al. | |
| 2008/0234812 A1 | 9/2008 | Pacetti | |
| 2008/0242171 A1 | 10/2008 | Huang et al. | |
| 2008/0281406 A1 | 11/2008 | Addonizio et al. | |
| 2008/0286321 A1 | 11/2008 | Reneker et al. | |
| 2008/0288044 A1 | 11/2008 | Osborne | |
| 2008/0305143 A1 | 12/2008 | Chen et al. | |
| 2008/0319535 A1 | 12/2008 | Craven et al. | |
| 2009/0012607 A1 | 1/2009 | Kim et al. | |
| 2009/0018643 A1 | 1/2009 | Hashi et al. | |
| 2009/0030499 A1 | 1/2009 | Bebb et al. | |
| 2009/0082846 A1 | 3/2009 | Chobotov | |
| 2009/0088828 A1 | 4/2009 | Shalev et al. | |
| 2009/0127748 A1 | 5/2009 | Takahashi | |
| 2009/0136651 A1 | 5/2009 | Larsen et al. | |

(56) References Cited

U.S. PATENT DOCUMENTS

| | | |
|---|---|---|
| 2009/0160099 A1 | 6/2009 | Huang |
| 2009/0163994 A1 | 6/2009 | Quigley et al. |
| 2009/0227944 A1 | 9/2009 | Weber |
| 2009/0232920 A1 | 9/2009 | Lozano et al. |
| 2009/0248131 A1 | 10/2009 | Greenan |
| 2009/0248144 A1 | 10/2009 | Bahler et al. |
| 2009/0269429 A1 | 10/2009 | Lozano et al. |
| 2009/0280325 A1 | 11/2009 | Lozano et al. |
| 2009/0319034 A1 | 12/2009 | Sowinski |
| 2010/0013126 A1 | 1/2010 | Ishaque et al. |
| 2010/0042198 A1 | 2/2010 | Burton |
| 2010/0042199 A1 | 2/2010 | Burton |
| 2010/0063574 A1 | 3/2010 | Bogert |
| 2010/0076543 A1 | 3/2010 | Melsheimer et al. |
| 2010/0093093 A1 | 4/2010 | Leong et al. |
| 2010/0129628 A1 | 5/2010 | Young |
| 2010/0190254 A1 | 7/2010 | Chian et al. |
| 2010/0233115 A1 | 9/2010 | Patel et al. |
| 2010/0280590 A1 | 11/2010 | Sun et al. |
| 2010/0304205 A1 | 12/2010 | Jo et al. |
| 2010/0323052 A1 | 12/2010 | Orr et al. |
| 2010/0331965 A1 | 12/2010 | Dugas et al. |
| 2011/0030885 A1 | 2/2011 | Anneaux et al. |
| 2011/0031656 A1 | 2/2011 | Anneaux et al. |
| 2011/0060276 A1 | 3/2011 | Schaeffer et al. |
| 2011/0087318 A1 | 4/2011 | Daugherty et al. |
| 2011/0089603 A1 | 4/2011 | Fabbricante et al. |
| 2011/0135806 A1 | 6/2011 | Grewe et al. |
| 2011/0142804 A1 | 6/2011 | Gaudette et al. |
| 2011/0156319 A1 | 6/2011 | Kurokawa et al. |
| 2011/0263456 A1 | 10/2011 | Harttig |
| 2011/0295200 A1 | 12/2011 | Speck et al. |
| 2011/0301696 A1 | 12/2011 | Mangiardi |
| 2012/0114722 A1 | 5/2012 | Ballard et al. |
| 2012/0201988 A1 | 8/2012 | Hansen et al. |
| 2012/0271396 A1 | 10/2012 | Zheng |
| 2012/0292810 A1 | 11/2012 | Peno et al. |
| 2012/0316633 A1 | 12/2012 | Flanagan et al. |
| 2013/0018220 A1 | 1/2013 | Vad |
| 2013/0023175 A1 | 1/2013 | Anneaux et al. |
| 2013/0053948 A1 | 2/2013 | Anneaux et al. |
| 2013/0059497 A1 | 3/2013 | Anneaux et al. |
| 2013/0079700 A1 | 3/2013 | Ballard et al. |
| 2013/0085565 A1 | 4/2013 | Eller et al. |
| 2013/0184808 A1 | 7/2013 | Hall et al. |
| 2013/0184810 A1 | 7/2013 | Hall et al. |
| 2013/0231733 A1 | 9/2013 | Knisley et al. |
| 2013/0238086 A1 | 9/2013 | Ballard et al. |
| 2013/0268062 A1 | 10/2013 | Puckett et al. |
| 2013/0316103 A1 | 11/2013 | Anneaux et al. |
| 2014/0012304 A1 | 1/2014 | Lampropoulos et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0265061 A1 | 9/2014 | Hall et al. |
| 2014/0273703 A1 | 9/2014 | Mower et al. |
| 2015/0081000 A1 | 3/2015 | Hossainy |
| 2015/0134051 A1 | 5/2015 | Donadio et al. |
| 2015/0320542 A1 | 11/2015 | Gabriele et al. |
| 2016/0250048 A1 | 9/2016 | Hall et al. |
| 2016/0331528 A1* | 11/2016 | Parker ............... A61L 27/18 |
| 2017/0360993 A1 | 10/2017 | Argentine et al. |
| 2018/0064565 A1 | 3/2018 | MacTaggart |
| 2019/0060528 A1 | 2/2019 | Skender et al. |
| 2019/0076276 A1 | 3/2019 | Longo |
| 2019/0110911 A1 | 4/2019 | Nae |
| 2020/0015987 A1 | 1/2020 | Einav |

FOREIGN PATENT DOCUMENTS

| | | |
|---|---|---|
| EP | 1605014 | 12/2005 |
| EP | 2363516 | 7/2011 |
| JP | 5140476 | 5/1975 |
| JP | 2007519491 | 7/2007 |
| JP | 2007531833 | 11/2007 |
| JP | 2009232882 | 10/2009 |
| JP | 2010517625 | 5/2010 |
| JP | 2010540190 | 12/2010 |
| KR | 20100077913 | 7/2010 |
| KR | 1020100108382 | 10/2010 |
| WO | 199800090 | 1/1998 |
| WO | 2003051233 | 6/2003 |
| WO | 2004090206 | 10/2004 |
| WO | 2005018600 | 3/2005 |
| WO | 2005074547 | 8/2005 |
| WO | 2005098100 | 10/2005 |
| WO | 2006123340 | 11/2006 |
| WO | 2007075256 | 7/2007 |
| WO | 2008097592 | 8/2008 |
| WO | 2009046372 | 4/2009 |
| WO | 2009127170 | 10/2009 |
| WO | 2009146280 | 12/2009 |
| WO | 2010083530 | 7/2010 |
| WO | 2010132636 | 11/2010 |
| WO | 2011017698 | 2/2011 |
| WO | 2012103501 | 8/2012 |
| WO | 2012122485 | 9/2012 |
| WO | 2013109528 | 7/2013 |
| WO | 2014007979 | 1/2014 |

OTHER PUBLICATIONS

Office Action dated Jan. 2, 2009 for U.S. Appl. No. 13/360,444.
Office Action dated Jan. 2, 2019 for U.S. Appl. No. 14/152,590.
European Search Report dated Feb. 12, 2016 for EP13813055.4.
European Search Report dated Mar. 30, 2016 for EP13838784.0.
European Search Report dated Aug. 19, 2014 for EP12755426.9.
European Search Report dated Sep. 6, 2016 for EP14774594.7.
Extended European Search Report dated Mar. 30, 2016 for EP13838578.6.
Extended European Search Report dated Jun. 25, 2015 for EP12739348.6.
International Preliminary Report dated Mar. 24, 2015 for PCT/US2013/060812.
International Preliminary Report dated Jul. 30, 2013 for PCT/US2012/023006.
International Report on Patentability dated Jul. 22, 2014 for PCT/US2013/021554.
International Search Report and Written Opinion dated Apr. 26, 2013 for PCT/US2013/021554.
International Search Report and Written Opinion dated May 23, 2012 for PCT/US2012/023006.
International Search Report and Written Opinion dated Jun. 8, 2016 for PCT/US2016/019487.
International Search Report and Written Opinion dated Jun. 26, 2014 for PCT/US2014/024868.
International Search Report and Written Opinion dated Jul. 1, 2014 for PCT/US2014/023416.
International Search Report and Written Opinion dated Sep. 6, 2013 for PCT/US2013/046245.
International Search Report and Written Opinion dated Dec. 3, 2013 for PCT/US2013/060172.
International Search Report and Written Opinion dated Dec. 5, 2013 for PCT/US2013/060812.
Notice of Allowance dated Jan. 25, 2017 for U.S. Appl. No. 14/152,626.
Notice of Allowance dated Jul. 11, 2016 for U.S. Appl. No. 13/826,618.
Notice of Allowance dated Sep. 3, 2015 for U.S. Appl. No. 13/787,327.
Notice of Allowance dated Oct. 4, 2017 for U.S. Appl. No. 14/204,466.
Office Action dated Jan. 12, 2016 for U.S. Appl. No. 14/152,590.
Office Action dated Jan. 13, 2015 for U.S. Appl. No. 13/827,790.
Office Action dated Jan. 16, 2018 for U.S. Appl. No. 14/081,715.
Office Action dated Jan. 22, 2016 for U.S. Appl. No. 14/152,626.
Office Action dated Jan. 23, 2017 for U.S. Appl. No. 14/081,715.
Office Action dated Feb. 4, 2015 for U.S. Appl. No. 13/360,444.
Office Action dated Feb. 7, 2017 for U.S. Appl. No. 13/827,790.
Office Action dated Feb. 20, 2015 for U.S. Appl. No. 14/044,050.

(56) References Cited

OTHER PUBLICATIONS

Office Action dated Feb. 22, 2016 for U.S. Appl. No. 13/742,077.
Office Action dated Feb. 26, 2015 for U.S. Appl. No. 14/152,590.
Office Action dated Mar. 3, 2014 for U.S. Appl. No. 13/742,025.
Office Action dated Mar. 15, 2017 for U.S. Appl. No. 14/207,344.
Office Action dated Mar. 28, 2016 for U.S. Appl. No. 13/827,790.
Office Action dated Mar. 31, 2017 for U.S. Appl. No. 14/204,466.
Office Action dated Apr. 7, 2017 for U.S. Appl. No. 13/826,618.
Office Action dated Apr. 27, 2017 for U.S. Appl. No. 13/742,077.
Office Action dated May 9, 2014 for U.S. Appl. No. 13/360,444.
Office Action dated May 19, 2017 for U.S. Appl. No. 13/742,025.
Office Action dated Jun. 8, 2016 for U.S. Appl. No. 14/044,050.
Office Action dated Jun. 9, 2016 for U.S. Appl. No. 14/152,626.
Office Action dated Jun. 19, 2017 for U.S. Appl. No. 14/081,504.
Office Action dated Jun. 23, 2017 for U.S. Appl. No. 13/829,493.
Office Action dated Jun. 29, 2017 for U.S. Appl. No. 14/081,715.
Office Action dated Jun. 30, 2016 for U.S. Appl. No. 14/081,715.
Office Action dated Jul. 2, 2014 for U.S. Appl. No. 14/044,050.
Office Action dated Jul. 12, 2017 for U.S. Appl. No. 15/053,232.
Office Action dated Jul. 26, 2017 for U.S. Appl. No. 13/827,790.
Office Action dated Jul. 29, 2015 for U.S. Appl. No. 14/152,626.
Office Action dated Aug. 10, 2015 for U.S. Appl. No. 14/044,050.
European Search Report dated Dec. 6, 2018 for EP13813055.4.
Office Action dated Jan. 14, 2019 for U.S. Appl. No. 13/827,790.
Office Action dated Jan. 17, 2019 for U.S. Appl. No. 14/832,422.
Office Action dated Jan. 25, 2019 for U.S. Appl. No. 14/207,344.
Office Action dated Feb. 8, 2019 for U.S. Appl. No. 14/081,715.
Office Action dated Jun. 15, 2018 for U.S. Appl. No. 14/207,344.
Office Action dated Jun. 28, 2018 for U.S. Appl. No. 14/081,715.
Office Action dated Jul. 13, 2018 for U.S. Appl. No. 13/827,790.
Office Action dated Jul. 26, 2018 for U.S. Appl. No. 14/152,590.
Office Action dated Aug. 6, 2018 for U.S. Appl. No. 13/360,444.
Notice of Allowance dated Apr. 3, 2018 for U.S. Appl. No. 14/081,504.
Notice of Allowance dated May 9, 2018 for U.S. Appl. No. 15/053,232.
Office Action dated Feb. 16, 2018 for U.S. Appl. No. 13/742,077.
Office Action dated May 11, 2018 for U.S. Appl. No. 13/826,618.
Office Action dated May 11, 2018 for U.S. Appl. No. 14/832,422.
Ep Examination Report dated May 28, 2019 for EP12755426.9.
Notice of Allowance dated Oct. 9, 2019 for U.S. Appl. No. 13/826,618.
Office Action dated Aug. 22, 2019 for U.S. Appl. No. 14/207,344.
Office Action dated Oct. 7, 2019 for U.S. Appl. No. 13/360,444.
Office Action dated Oct. 7, 2019 for U.S. Appl. No. 14/152,590.
Office Action dated Jul. 11, 2019 for U.S. Appl. No. 14/081,715.
Notice of Allowance dated Jan. 30, 2020 for U.S. Appl. No. 14/152,590.
Notice of Allowance dated Feb. 6, 2020 for U.S. Appl. No. 13/360,444.
Notice of Allowance dated Mar. 13, 2020 for U.S. Appl. No. 14/832,422.
Office Action dated Mar. 25, 2020 for U.S. Appl. No. 14/081,715.
Office Action dated Apr. 6, 2020 for U.S. Appl. No. 13/827,790.
Office Action dated Apr. 29, 2020 for U.S. Appl. No. 14/207,344.
Office Action dated May 1, 2020 for U.S. Appl. No. 16/035,334.
European Search Report dated Jun. 16, 2014 for EP14160501.
International Search Report dated Dec. 3, 2013 for PCT/US2013/060172.
Notice of Allowance dated Aug. 7, 2020 for U.S. Appl. No. 14/207,344.
Notice of Allowance dated Dec. 14, 2020 for U.S. Appl. No. 14/081,715.
European Search Report dated Dec. 23, 2020 for EP20199088.4.
Office Action dated Dec. 23, 2020 for U.S. Appl. No. 13/827,790.
Yasuda, et al., Contact Angle of Water on Polymer Surfaces, Am Chem, Langmuir, vol. 10 No. 7 ,1994.

* cited by examiner

METHODS, SYSTEMS, AND APPARATUSES FOR MANUFACTURING ROTATIONAL SPUN APPLIANCES

RELATED APPLICATIONS

This application is a divisional application of U.S. patent application Ser. No. 14/204,466, filed on Mar. 11, 2014 and titled, METHODS, SYSTEMS, AND APPARATUSES FOR MANUFACTURING ROTATIONAL SPUN APPLIANCES, which claims priority to U.S. Provisional Application No. 61/780,524 filed on Mar. 13, 2013, titled METHODS, SYSTEMS, AND APPARATUSES FOR MANUFACTURING ROTATIONAL SPUN APPLIANCES, the entire contents of both of which are hereby incorporated by reference.

TECHNICAL FIELD

The present disclosure relates generally to rotational spun materials. More specifically, the present disclosure relates to methods and systems for manufacturing rotational spun appliances. Even more specifically, the rotational spun appliances are medical appliances or other prostheses made of, constructed from, covered or coated with rotational spun materials, such as polytetrafluoroethylene (PTFE).

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings are not necessarily drawn to scale unless specifically indicated. These drawings depict only typical embodiments, which will be described with additional specificity and detail through use of the accompanying drawings in which:

DETAILED DESCRIPTION

Figure 1A:
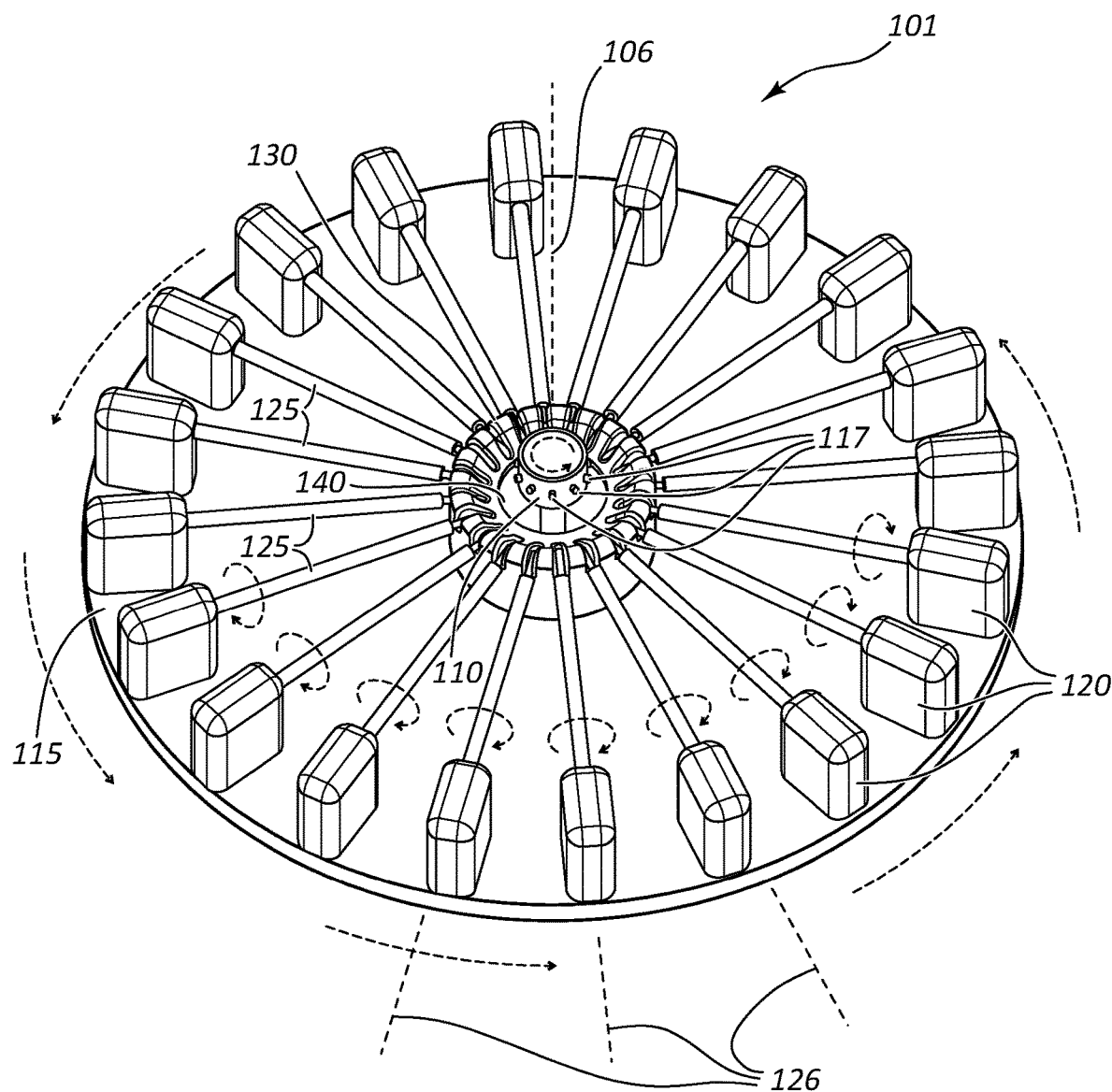
FIG. 1A is a perspective view of one embodiment of a rotational spinning apparatus.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments.

Medical appliances may be deployed in various body lumens for a variety of purposes. Stents may be deployed, for example, in the central venous system for a variety of therapeutic purposes including the treatment of occlusions within the lumens of that system. The current disclosure may be applicable to stents or other medical appliances designed for the central venous system, peripheral vascular stents, abdominal aortic aneurism stents, bronchial stents, esophageal stents, biliary stents, coronary stents, gastrointestinal stents, neuro stents, thoracic aortic endographs, or any other stent or stent graft. Further, the present disclosure may be equally applicable to other prosthesis such as stent grafts or grafts.

For convenience, many of the specific examples included below reference stents and/or grafts. Notwithstanding any of the particular medical appliances referenced in the examples or disclosure below, the disclosure and examples may apply analogously to any tubular prostheses or other tubular medical appliance.

As used herein, the term "stent" refers to a medical appliance configured for use within a bodily structure, such as within a body lumen. A stent may comprise a scaffolding or support structure, such as a frame, and/or a covering. Thus, as used herein, "stent" refers to both covered and uncovered scaffolding structures.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations. For example, the proximal end of a mandrel is defined as the end closest to the actuator rotating the mandrel. The distal end is the end opposite the proximal end, along the longitudinal direction of the mandrel.

In embodiments where a stent or another appliance is composed of a metal wire structure coupled to one or more layers of a film or sheet-like components, such as a polymer layer, the metal structure is referred to as the "scaffolding" or "frame," and the polymer layer as the "covering" or "coating." The terms "covering" or "coating" may refer to a single layer of polymer, multiple layers of the same polymer, or layers comprising distinct polymers used in combination. Furthermore, as used herein, the terms "covering" and "coating" refer only to a layer or layers which are coupled to a portion of the scaffold; neither term requires that the entire scaffold be "covered" or "coated." In other words, medical appliances wherein a portion of the scaffold may be covered and a portion remains bare are within the scope of this disclosure. Finally, any disclosure recited in connection with coverings or coatings may analogously be applied to medical devices comprising one or more "covering" layers with no associated frame or other structure.

Medical device coverings may comprise multilayered constructs, comprised of two or more layers which may be serially applied. Further, multilayered constructs may comprise nonhomogeneous layers, meaning adjacent layers have differing properties. Thus, as used herein, each layer of a multilayered construct may comprise a distinct layer, either due to the distinct application of the layers or due to differing properties between layers.

Additionally, as used herein, "tissue ingrowth" or "cellular penetration" refers to any presence or penetration of a biological or bodily material into a component of a medical appliance. For example, the presence of body tissues (e.g., collagen, cells, and so on) within an opening or a pore of a layer or component of a medical appliance comprises tissue ingrowth into that component.

Further, as used herein, "attachment" of tissue to a component of a medical appliance refers to any bonding or adherence of a tissue to the appliance, including indirect bonds. For example, tissue of some kind (e.g., collagen) may become attached to a stent or graft covering (including attachment via tissue ingrowth) and another layer of biologic material (such as endothelial cells) may, in turn, adhere to the first tissue. In such instances, the second biologic material (endothelial cells in the example) and the tissue (collagen in the example) are "attached" to the stent or graft covering.

Furthermore, throughout the present disclosure, certain rotational spun materials may be referred to as inhibiting or promoting certain biological responses. These relative terms are intended to reference the characteristics of rotational spun materials made utilizing the disclosed methods, systems, and apparatuses as compared with respect to other materials or coatings.

Rotational spinning refers generally to processes involving the expulsion of flowable material from one or more orifices, the material forming fibers which are subsequently deposited on a mandrel. Examples of flowable materials include dispersions, solutions, suspensions, liquids, molten or semi-molten material, and other fluid or semi-fluid materials. In some embodiments, the rotational spinning processes are completed in the presence or absence of an electric field.

One example of a rotational spinning process comprises loading a polymer solution or dispersion into a cup or spinneret configured with orifices on the outside circumference of the spinneret. The spinneret is then rotated, causing (through a combination of centrifugal and hydrostatic forces, for example) the flowable material to be expelled from the orifices. The material may then form a "jet" or "stream" extending from the orifice, with drag forces tending to cause the stream of material to elongate into a small-diameter fiber. The fibers may then be deposited on a collection apparatus. Exemplary methods and systems for rotational spinning can be found in U.S. Patent Publication No. US2009/0280325, titled "Methods and Apparatuses for Making Superfine Fibers," the contents of which are herein incorporated by reference in their entirety.

The present disclosure relates to methods of making a rotational spun appliance. In some embodiments, the methods comprise rotating a spinneret around a first axis to produce spinning fibers. The methods further comprise rotating a plurality of mandrels, each of the mandrels rotating about its own axis, wherein each mandrel's own axis of rotation is not the same as the first axis of rotation. The methods further comprise contacting the spinning fibers with the rotating mandrels, such that fibers are deposited on the mandrels.

The methods may further comprise collectively and simultaneously rotating the plurality of mandrels around the first axis of rotation.

In some embodiments, each mandrel's own axis of rotation is perpendicular to the first axis of rotation. The rotation of each mandrel around its own axis of rotation may result in the surface of the mandrel turning in the same direction as the spinning fibers are spinning. The rotation of each mandrel around its own axis of rotation may result in the surface of the mandrel turning in an opposite direction as the spinning fibers are spinning.

In some embodiments, each mandrel's own axis of rotation is radially tangential to the first axis of rotation.

In some embodiments, the rotation of the plurality of mandrels around the first axis of rotation is in the same direction as the rotation of the spinneret. In other embodiments, the rotation of the plurality of mandrels around the first axis of rotation is in the opposite direction as the rotation of the spinneret.

In some embodiments, the plurality of mandrels are removable from the field of fibers produced by the spinneret during startup and shutdown of rotation of the spinneret. In such embodiments, the rotation of each of the plurality of mandrels around its own axis and around the first axis is startable and stoppable while the plurality of mandrels are removed from the field of fibers produced by the spinneret.

In some embodiments, the methods further comprise placing fiber-wrapped mandrels in a sintering oven and sintering the fiber-wrapped mandrels.

Rotational spinning may be configured to create tubular structures comprised of elongate fibers, including nanofibers (i.e., fibers which are smaller than one micron in diameter) or microfibers (i.e., fibers which are between one micron and one millimeter in diameter). In some instances the fibers are randomly disposed, while in other embodiments the alignment or orientation of the fibers is somewhat controlled or follows a general trend or pattern. Regardless of any pattern or degree of fiber alignment, as the fibers are deposited on a mandrel or on previously deposited fibers, the fibers are not woven, but rather are serially deposited on the mandrel or other fibers. Because rotational spinning may be configured to create a variety of structures, as used herein, the term "non-woven material" is intended to be broadly construed as referring to any rotational spun structure.

FIG. 1A illustrates a rotational spinning apparatus 101. The illustrated apparatus 101 comprises a spinneret 110 disposed near the center of a generally circular surface, such as disk 115. In the illustrated embodiment, disk 115 forms a ring around spinneret 110. Spinneret 110 further comprises orifices 117 located around the circumference of spinneret 110 and an internal reservoir. The illustrated apparatus 101 further comprises actuators 120 mounted on the upper surface of disk 115. Mandrels 125 extend from actuators 120 toward the radial center of disk 115. A support member rotatably engages the ends of mandrels 125 and supports each of mandrels 125.

Spinneret 110 is configured to rotate around a first axis of rotation 106. The internal reservoir is configured to be filled with a flowable material. In some instances polymer dispersions, including aqueous dispersions or polymer solutions, are used as the flowable material. Spinneret 110 is configured to be rotated such that the flowable material is forced out of the orifices 117. Molecules, including polymer chains, may tend to disentangle and/or align as the material is forced through the orifice 117. Additionally, in some embodiments the orifice 117 comprises a needle or nozzle that extends from the outside circumference of spinneret 110. Still further, in some embodiments the orifice 117 may comprise a cannula configured with a quick connection, such as a luer connection, allowing for rapid exchange of various cannula sizes. Any spinneret known in the art may be used, such as those disclosed in U.S. Patent Publication No. US2009/0280325 referenced above.

In some embodiments, spinneret 110 is configured to be rotated at about 500 rotations per minute (RPM) to about 25,000 RPM. It is known in the art what rotational speeds may be used to develop a particular fiber from a particular flowable material. Any spinneret rotational speed compatible with a desired fiber may be used. The fibers may loop completely around spinneret 110 one or more times before contacting mandrels 125.

Disk 115 is configured to rotate separately from spinneret 110 but around the same first axis of rotation 106. Disk 115 may be configured for selectively rotating in the same direction or the opposite direction as spinneret 110. In FIG. 1A, both spinneret 110 and disk 115 are illustrated as rotating counter-clockwise around first axis of rotation 106. In some embodiments, disk 115 is selectively configured for rotating at a slower speed than spinneret 110. Disk 115 may be configured for rotating at speeds of 1 to 1,000 RPM. In some embodiments, disk 115 may be configured for rotating at speeds of 1 to 900 RPM, 1 to 800 RPM, 1 to 700 RPM, 1 to 600 RPM, and 1 to 500 RPM. The diameter of disk 115 may be determined by the length of mandrels 125, which in turn may be determined by the desired length of medical appliances made upon mandrels 125.

Disk 115 comprises an opening 140 configured to allow access for spinneret 110. Disk 115 may be lifted away from spinneret 110 as disk 115 is separated from apparatus 101 for placement in a sintering oven. Alternatively, mandrels 125 may be separable from disk 115 and placed in the sintering oven without disk 115.

Actuators 120 are mounted on disk 115 and configured to rotate mandrels 125. Actuators 120 are configured to rotate with disk 115 as it rotates relative to spinneret 110. Each actuator 120 may comprise an electric motor, such as, for example, a direct-current stepper motor, for rotating a mandrel 125. The motor may be configured to handle sintering temperatures for when disk 115 is removed from rotational spinning apparatus 101 and placed in a sintering oven. Any method of transferring power to any electric motors of actuators 120 may be used. For example, the electric motors may be battery powered or wirelessly powered. In another example, the electric motors may be powered by rotating electrical contacts mounted beneath disk 115 that maintain communication with stationary electrical contacts while disk 115 rotates.

Alternatively, each actuator 120 may comprise a gear drive for rotating a mandrel 125. Each gear drive may be configured to handle sintering temperatures for when disk 115 is removed from rotational spinning apparatus 101 and placed in a sintering oven. Each gear drive may comprise a right angle gear drive for operably coupling the shaft of mandrel 125 to a power source. Each gear drive of an actuator 120 may have its own power source, such as an electric motor mounted beneath disk 115. In that embodiment, the electric motors may be configured in a ring beneath disk 115. The ring may be configured to rotate with disk 115. The ring may further be configured to be separable from disk 115 prior to disk 115 being placed in a sintering oven so that the motors are not placed in the sintering oven. Similar to the electric motors discussed previously, any method of transferring power to the electric motors may be used. For example, the electric motors may be battery powered, wirelessly powered, or powered by rotating electrical contacts that maintain communication with stationary electrical contacts while disk 115 rotates.

In another variation of the gear drive embodiment, all or multiple gear drives of the actuators 120 may be operably connected to a single power source. For example, a single electric motor may be mounted beneath disk 115. The motor may be operably connected to each of the actuators 120, such as via a belt and pulley system. The motor and/or the belt and pulley system may be separable from disk 115 prior to disk 115 being placed in a sintering oven.

Mandrels 125 are operably connected to actuators 120 and configured for rotation by actuators 120. Mandrels 125 may be selectively rotated in a forward or reverse direction around its own axis of rotation 126. In FIG. 1A, mandrels 125 are illustrated as rotating in the forward direction relative to actuators 120. In the illustrated embodiment, rotation of mandrels 125 in the forward direction results in the surface of mandrels 125 turning in the same direction as the spinning fibers are rotating. In other embodiments, mandrels 125 are rotated in the reverse direction of that illustrated. The reverse direction would result in the surface of mandrels 125 turning in the opposite direction from the direction the spinning fibers are rotating.

In some instances, mandrels 125 rotate at rates between about 1 RPM and about 3,000 RPM, including rates from about 100 RPM to about 2,000 RPM, including about 1,500 RPM, or about 50 RPM to about 300 RPM, including about 150 RPM. In some instances, the rotational speed of one or more of mandrels 125 is related to the rate at which spinneret 110 produces fibers. For example, in some embodiments, faster mandrel 125 rotational speed may be correlated with higher total fiber production rates for spinneret 110. In some embodiments, all of mandrels 125 turn at about the same speed. In other embodiments, some or all of mandrels 125 turn at different speeds.

FIG. 1A illustrates mandrels 125 as essentially cylindrical in shape. It should be understood that the diameter of mandrels 125 may be selected based on the desired inner diameter of a medical appliance. Additionally, mandrels 125 may have a shape other than cylindrical. For example, mandrels 125 may have a concave or convex shape, such that the ends of the resulting medical appliance, such as a stent or graft, have ends that are either wider or narrower than the middle of the appliance.

The surface of mandrels 125 is illustrated as smooth. The surface of mandrels 125 may have any texture or surface profile desired. For example, mandrels 125 may have corrugated ridges and grooves that wrap around the surface of mandrels 125. The ridges and grooves may impart additional structural strength in a medical appliance made with mandrels 125.

Furthermore, in some embodiments, one or more of mandrels 125 may be configured for use in connection with a vacuum system. For example, openings in the surface of mandrels 125, such as micropores, may tend to draw fibers toward mandrels 125 in instances where the interior of mandrels 125 has lower pressure than the exterior of mandrels 125. Likewise, in some embodiments, one or more of mandrels 125 may have an electrostatic charge suitable for attracting fibers to mandrels 125.

Apparatus 101 is illustrated as having twenty mandrels 125. Apparatus 101 may have any number of mandrels depending upon factors such as the desired space between mandrels 125, radius of disk 115, and/or desired length, shape, and width of mandrels 125. In FIG. 1A, each mandrel's 125 own axis of rotation 126 is parallel to the upper surface of disk 115. In FIG. 1A, each mandrel's 125 own axis of rotation 126 is also perpendicular to first axis of rotation 106, such that the longitudinal axis of each of mandrels 125 extends radially from opening 140 of disk 115. Therefore, each mandrel's 125 own axis of rotation 126 is radially different from each other.

In a variation of the illustrated embodiment of FIG. 1A, mandrels 125 may not be oriented parallel to the upper surface of disk 115. For example, mandrels 125 may be oriented perpendicular to the upper surface of disk 115. In that example, mandrels 125 would be vertically oriented and each mandrel's own axis of rotation 126 would be parallel to first axis of rotation 106. Additionally, combinations of mandrels 125 in a variety of orientations may be used simultaneously on a single disk 115.

Support member is configured to support the distal ends of mandrels 125. FIG. 1A illustrates support member as a cylindrical hub protruding upward from the upper surface of disk 115. In FIG. 1A, spinneret 110 extends through the hollow center of support member. Support member may comprise any number of structures and/or shapes for supporting the distal ends of mandrels 125. For example, instead of a cylindrical hub, support member may comprise separate posts extending upward from the upper surface of disk 115. Each post may support the distal end of a single mandrel 125 and allow rotation of that mandrel 125.

The apparatus 101 may be utilized to create tubular structures of rotational spun fibers deposited on mandrels 125. As the dispersion is expelled from the internal reservoir of spinneret 110, drag or other aerodynamic forces acting on the stream or jet of material may cause the stream of dispersion to elongate and bend, forming a relatively small-diameter fiber of material. In some instances drag may be a shear force with respect to the stream. Additionally, certain components of the dispersion, such as the dispersion medium or solvent, may partially or fully evaporate as the material is drawn into fibers. In embodiments utilizing flowable materials which have no solvent, such as molten material, there may be no evaporation as the material is drawn into fibers.

The fibers eventually contact, and are deposited on, mandrels 125. The combination of forces described above may interact as the fibers are deposited, causing the fibers to be disposed in random patterns at a uniform thickness across the surface of mandrels 125, particularly when mandrels 125 are oriented horizontally as illustrated in FIG. 1A.

Figure 1B:
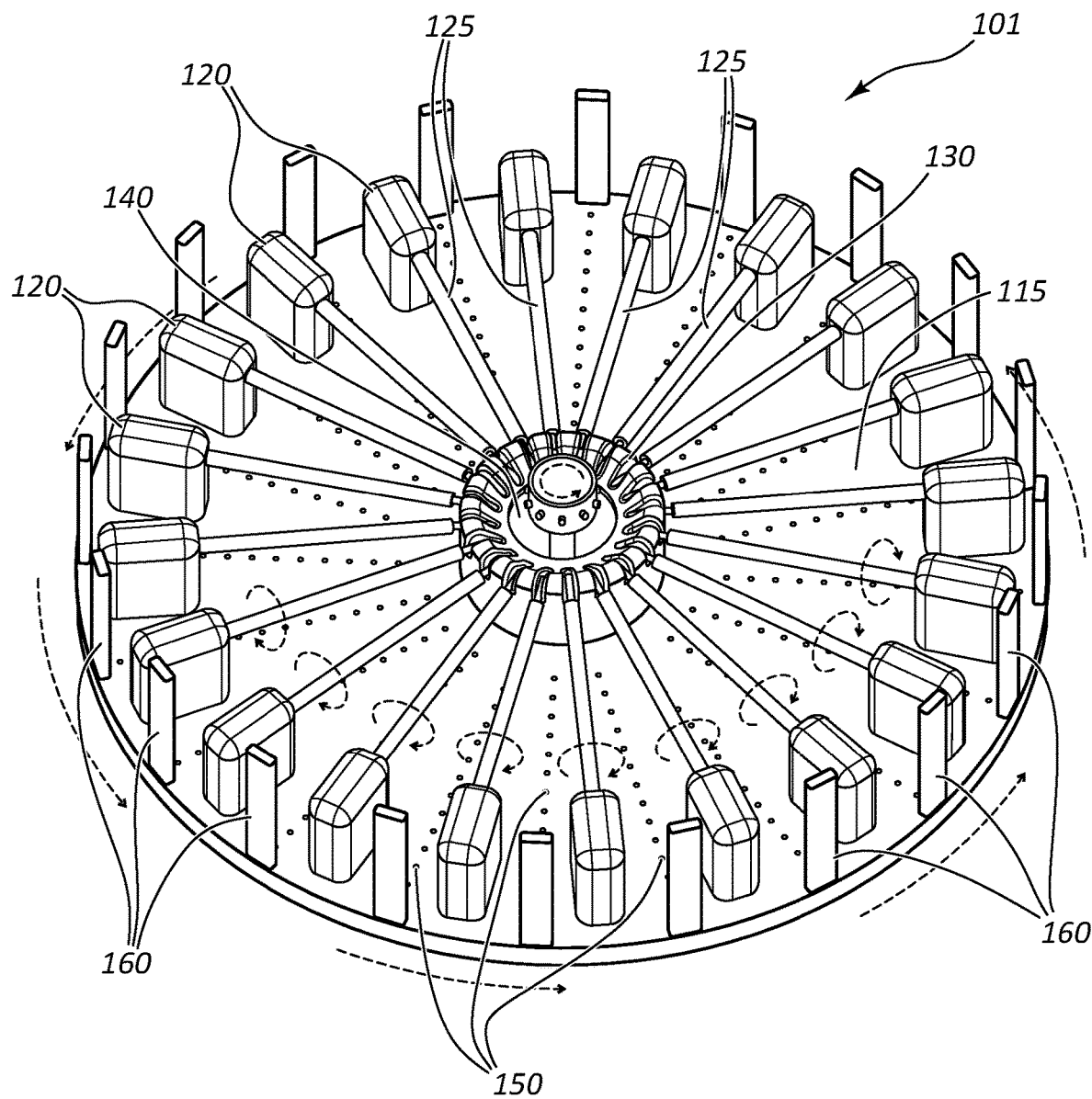
FIG. 1B is a perspective view of a variation of the embodiment illustrated in FIG. 1A.

FIG. 1B illustrates a variation of disk 115 that further comprises vents 150 that perforate disk 115. In this embodiment, air may be blown through vents 150 to introduce air currents that partially control the deposition of the fibers on mandrels 125. Vents 150 are illustrated as a radial array of pinholes in disk 115. There may be any number of vents 150 arrayed in any pattern. Additionally, other structures and devices for introducing air currents to the fibers may be used. For example, vents 150 may be flaps angled upward from the surface of disk 115, instead of air holes. The flaps may be configured so that as disk 115 rotates at a desired speed the desired air currents are generated.

FIG. 1B also illustrates a variation of disk 115 that further comprises shields 160. Shields 160 are configured to prevent rotating fibers from spinning beyond the perimeter of disk 115 and to prevent rotating fibers from becoming so long that the ends of fibers become entangled with each other and deposit on mandrels 125 as tangled clumps. Shields 160 are illustrated as flat rectangular pillars extending upward from the upper surface of disk 115. Shields 160 are also illustrated as located around the perimeter of disk 115. Shields 160 can align with vents 150. Air currents may be deflected along the inner surface of shields 160 and tend to deflect fibers from contacting shields 160.

Shields 160 may be of any shape compatible with preventing rotating fibers from spinning beyond the perimeter of disk 115. There may be any number of shields 160 in any pattern. For example, shields 160 may be a single continuous sheet or mesh that wraps around the perimeter of disk 115. Additionally, shields 160 may be configured to introduce air currents that direct rotating fibers toward mandrels 125. For example, shields 160 may be airfoils instead of pillars. The airfoils may be propeller-shaped and configured to generate air currents as disk 115 rotates, such that rotating fibers are pushed radially inward by the air currents toward mandrels 125.

FIGS. 2-7 illustrate apparatuses analogous to that shown in FIGS. 1A and 1B. It will be appreciated by one of skill in the art having the benefit of this disclosure that analogous components of the apparatuses may be interchangeable and that disclosure provided in connection with each embodiment may be applicable to the other and vice versa.

Figure 2:
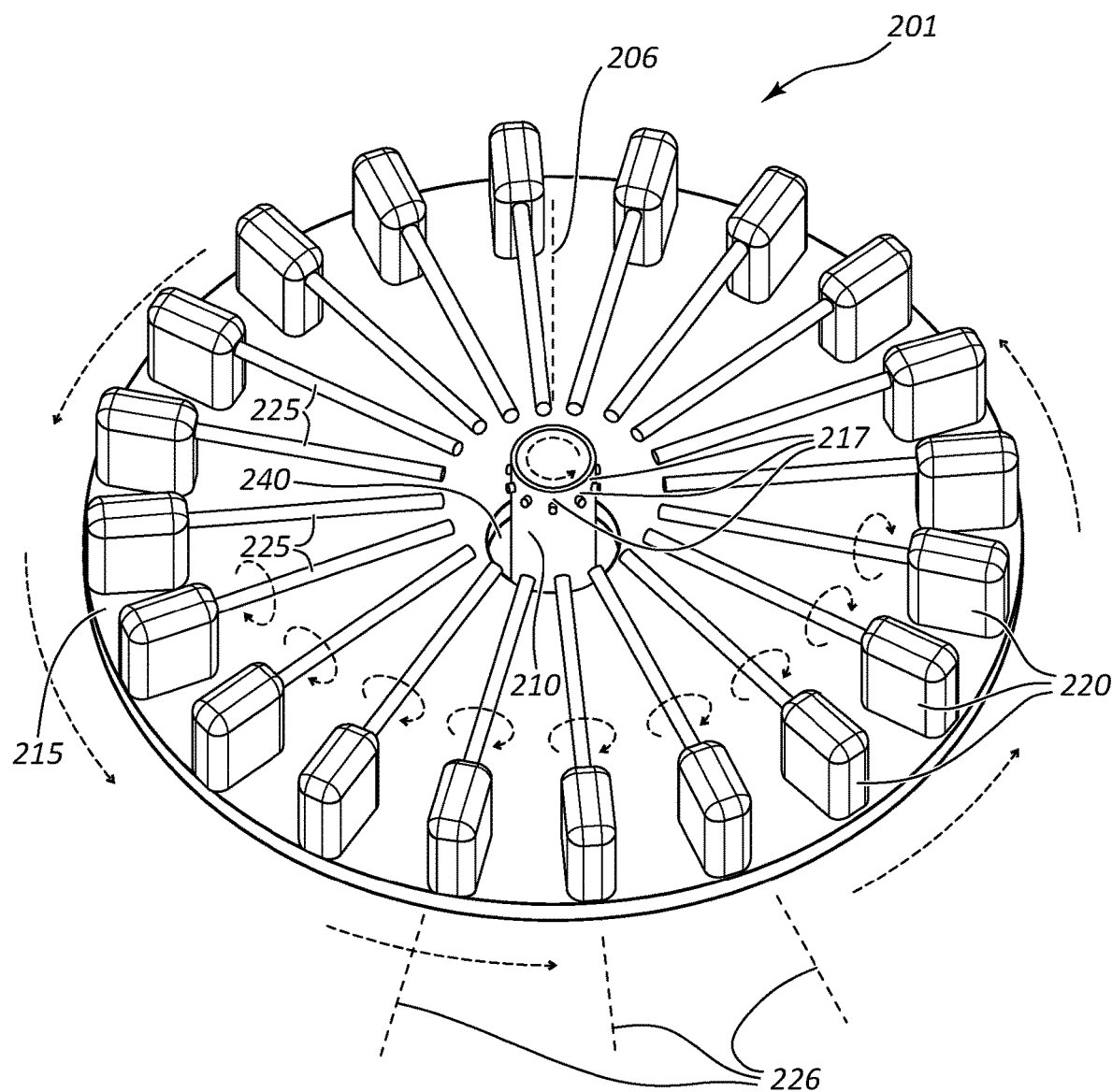
FIG. 2 is a perspective view of another embodiment of a rotational spinning apparatus.

FIG. 2 is a perspective view of a rotational spinning apparatus 201. Rotational spinning apparatus 201 includes a spinneret 210 comprising an internal reservoir and orifices 217. As compared to apparatus 101 of FIG. 1A, in the embodiment of FIG. 2 support member is not present and instead mandrels 225 are cantilevered from actuators 220. Disk 215 comprises opening 240 configured to allow access for spinneret 210.

Figure 3A:
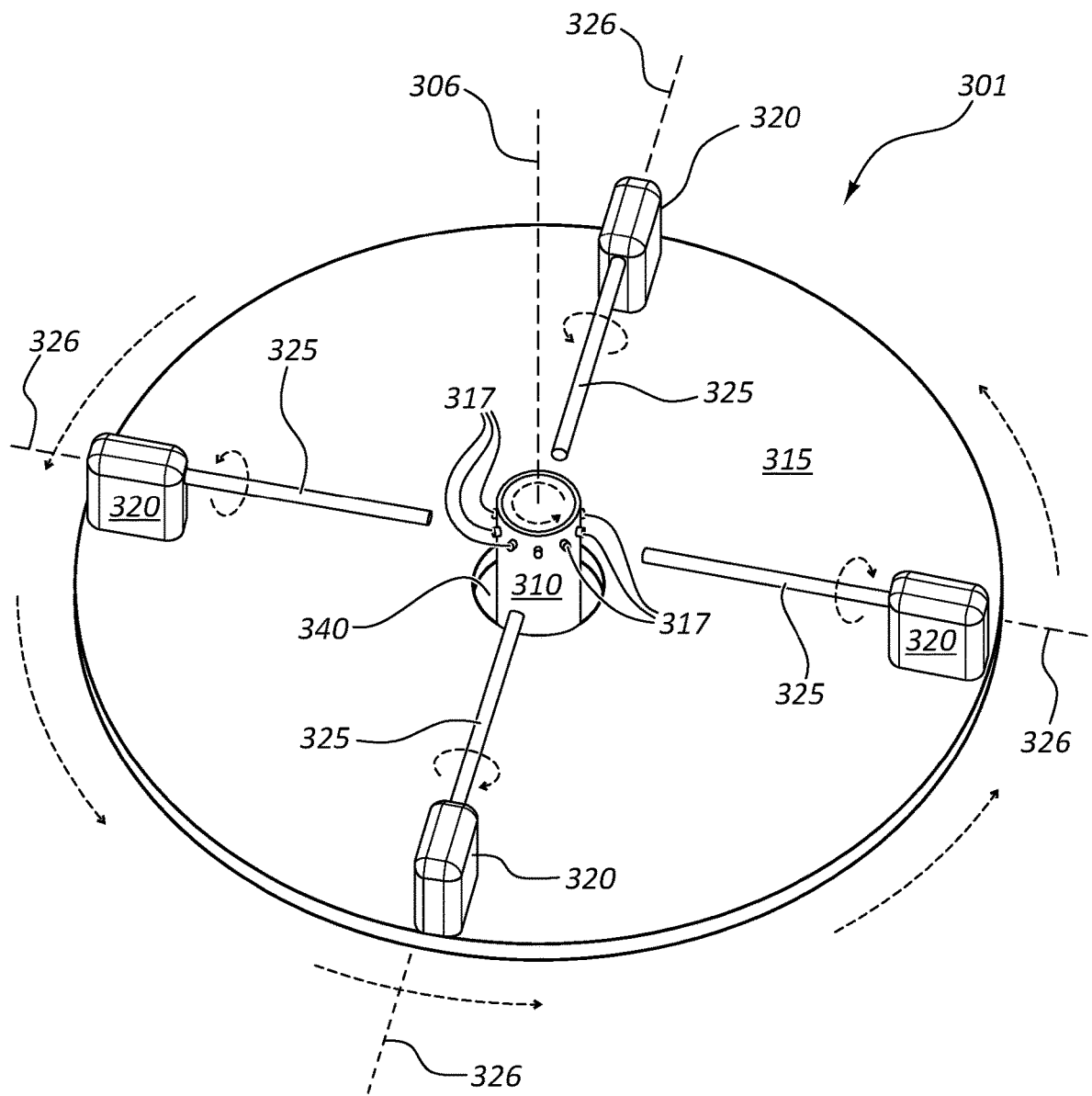
FIG. 3A is a perspective view of another embodiment of a rotational spinning apparatus.
Figure 3B:
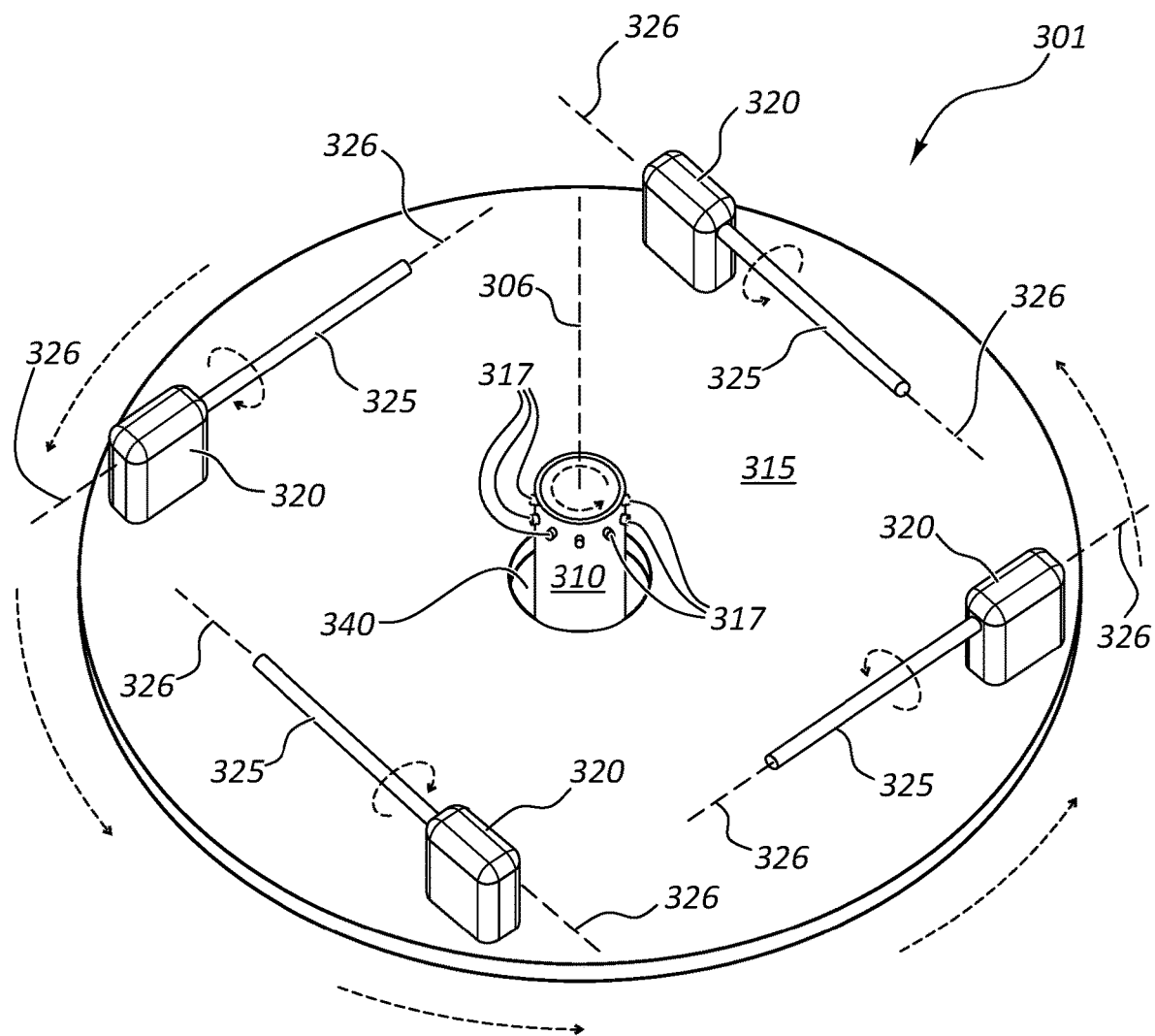
FIG. 3B is a perspective view of a variation of the embodiment illustrated in FIG. 3A.

FIGS. 3A and 3B are perspective views of a rotational spinning apparatus 301. Rotational spinning apparatus 301 includes a spinneret 310 comprising an internal reservoir and orifices 317. Similar to apparatus 201 of FIG. 2, the support member of apparatus 301 is not present and mandrels 325 are cantilevered from actuators 320.

In the illustrated embodiment of FIGS. 3A and 3B, only four mandrels 325 are present. More or less mandrels 325 may be present. In both FIGS. 3A and 3B, each mandrel's 325 own axis of rotation 326 is parallel to the upper surface of a disk 315. In FIG. 3A, each mandrel's 325 own axis of rotation 326 is perpendicular to a first axis of rotation 306. Or stated another way, the longitudinal axis of each of mandrels 325 extends radially from an opening 340 of disk 315. Each mandrel's 325 own axis of rotation 326 is radially different from each other. In FIG. 3B, each mandrel's 325 own axis of rotation 326 is radially tangential to first axis of rotation 306. Or stated another way, the longitudinal axis of each of mandrels 325 is oriented perpendicular to opening 340 in the center of disk 315.

In the illustrated embodiment of FIGS. 3A and 3B, actuators 320 may be configured to be pivotable to allow mandrels 325 to either extend radially from opening 340 in the center of disk 315 or to be oriented perpendicular to opening 340 in the center of disk 315. In other variations, actuators 320 may not be pivotable and instead disk 315 may have alternative mounting holes and actuators 320 may be mounted in various orientations.

Figure 3C:
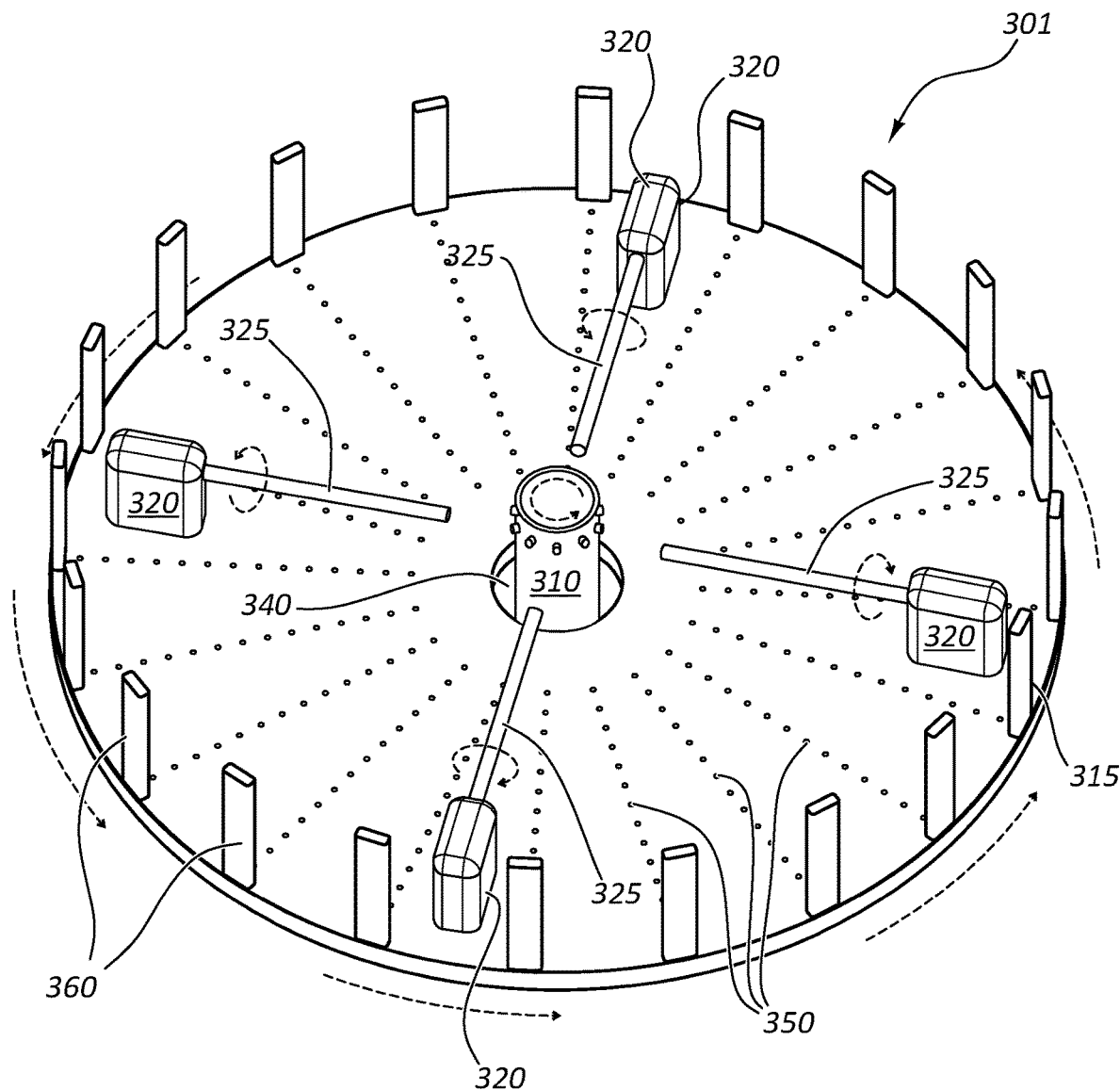
FIG. 3C is a perspective view of another variation of the embodiment illustrated in FIG. 3A.

In a variation of the embodiment illustrated in FIGS. 3B and 3C, mandrels 325 may be permanently oriented perpendicular to opening 340 at the center of disk 315. In another variation, mandrels 325 may be oriented at any angle relative to opening 340 at the center of disk 315. When mandrels 325 do not extend radially from opening 340 of disk 315 (i.e., each mandrel's 325 own axis of rotation 326 is not perpendicular to first axis of rotation 306, such as illustrated in FIG. 3B), then it may be possible to increase the length of mandrels 325 over that illustrated in FIGS. 3B and 3C.

In another variation of the embodiment illustrated in FIG. 3B, instead of mandrels 325 being cantilevered by actuators 320, the distal ends of mandrels 325 may be supported by individual supports, analogous to support member of apparatus 101.

FIG. 3C illustrates an embodiment similar to that illustrated in FIG. 1B, namely vents 350 and shields 360 are illustrated in FIG. 3C.

Figure 4:
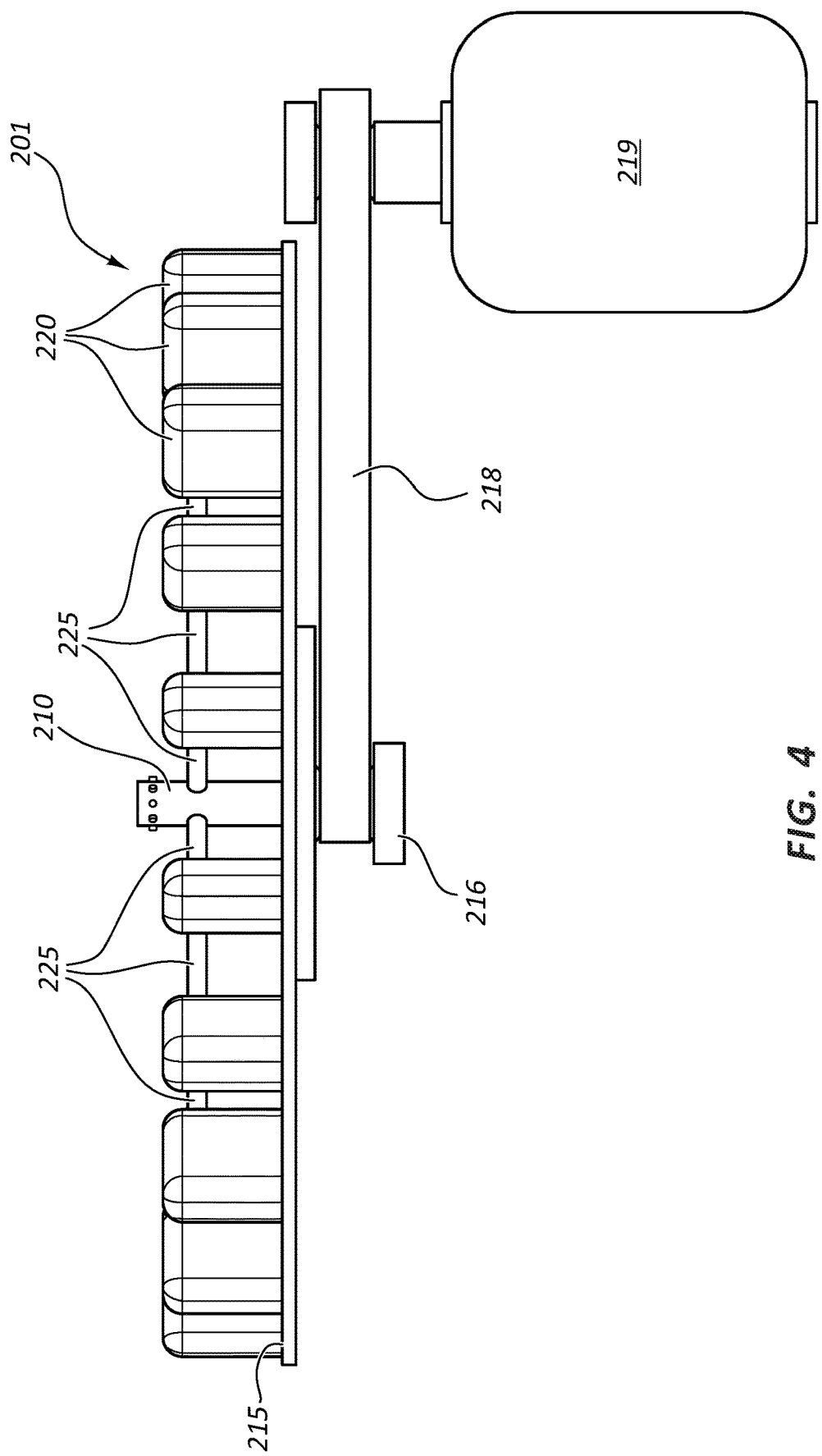
FIG. 4 is a side view of the embodiment illustrated in FIG. 2.

FIG. 4 illustrates a side view of apparatus 201 and illustrates one embodiment of a power source that may be used for rotating disk 215. FIG. 4 illustrates a belt drive system attached to the underside of disk 215. A drive 216 is attached to the underside of disk 215. Drive 216 is operably connected by a belt 218 to a power source 219. In the illustrated embodiment, power source 219 is an electric motor. Methods of rotating disks are known in the art. Any number of power sources and drive systems may be used to rotate disk 215. It should be understood that the discussion of FIG. 4 applies to any of the disclosed apparatuses, including apparatuses 101 and 301.

Apparatuses 201 (and also apparatuses 101 and 301 by analogy) may further be configured with a moveable slide configured to allow disk 215, drive 216, belt 218, and power source 219 to be slid away from spinneret 210. In such embodiments, spinneret 210 may not extend through opening 240. Instead spinneret 210 may be suspended above disk 215. In such embodiments, when disk 215 is in operational position, orifices 217 would still occupy the same geographical space relative to disk 215 as they do in FIG. 2. The moveable slide allows disk 215 and/or mandrels 225 to either start up or slow down rotation while separated from spinneret 210 and then be placed in the operating position when at operational speed. Likewise, spinneret 210 is able to reach operational speed and optimal fiber production before mandrels 225 are exposed to the produced fibers. Similarly, spinneret 210 would be able to cease fiber production without exposing mandrels 225 to suboptimal fibers.

Figure 5A:
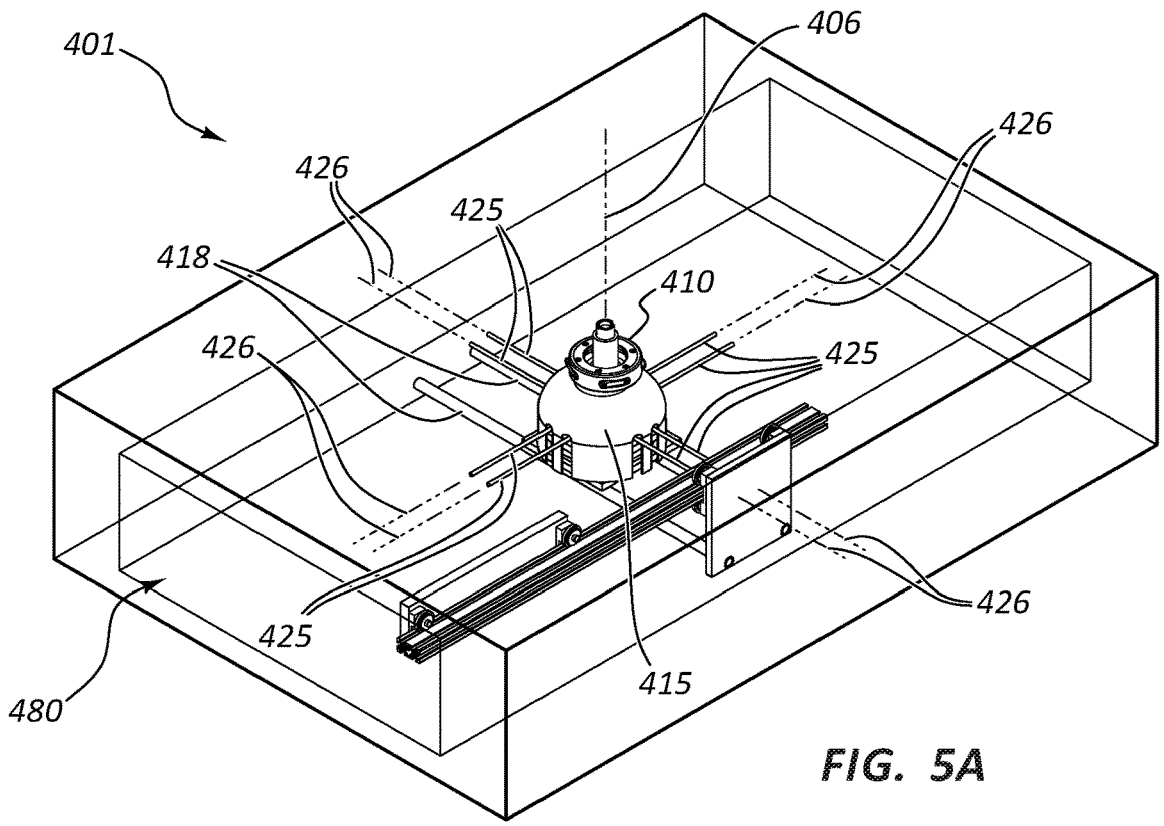
FIG. 5A a perspective view of another embodiment of a rotational spinning apparatus.

FIG. 5A illustrates a rotational spinning apparatus 401. Apparatus 401 comprises a hub 415 configured to rotate around a first axis of rotation 406. Apparatus 401 further comprises mandrels 425 operably connected to hub 415 and each configured for rotation by hub 415 around its own axis of rotation 426 that is not the same as first axis of rotation 406, such that during operation of apparatus 401, mandrels 425 are rotated around both first axis of rotation 406 and each mandrel's 425 own axis of rotation 426.

Apparatus 401 further comprises a spinneret 410 separate from hub 415 and configured to also rotate around first axis of rotation 406. Spinneret 410 includes orifices 417. Spinneret 410 may be operably coupled to an actuator (not shown) configured to rotate spinneret 410 above hub 415.

A difference between apparatus 401 and apparatuses 101, 201, and 301 is that the mandrels extend from a hub instead of being mounted on a disk. Additionally, the actuators for the mandrels are built into hub 415 in apparatus 401. It should be understood that analogous disclosure regarding apparatuses 101, 201, and 301 applies also to apparatus 401 and vice versa.

In the illustrated embodiment, hub 415 has eight mandrels 425 extending outwardly from it. Hub 415 may have any number of mandrels 425 extending outwardly from it. Likewise, hub 415 may have any structure compatible with rotating mandrels 425 around first axis of rotation 406 and also rotating each of mandrels 425 around its own axis of rotation 426.

Figure 5B:
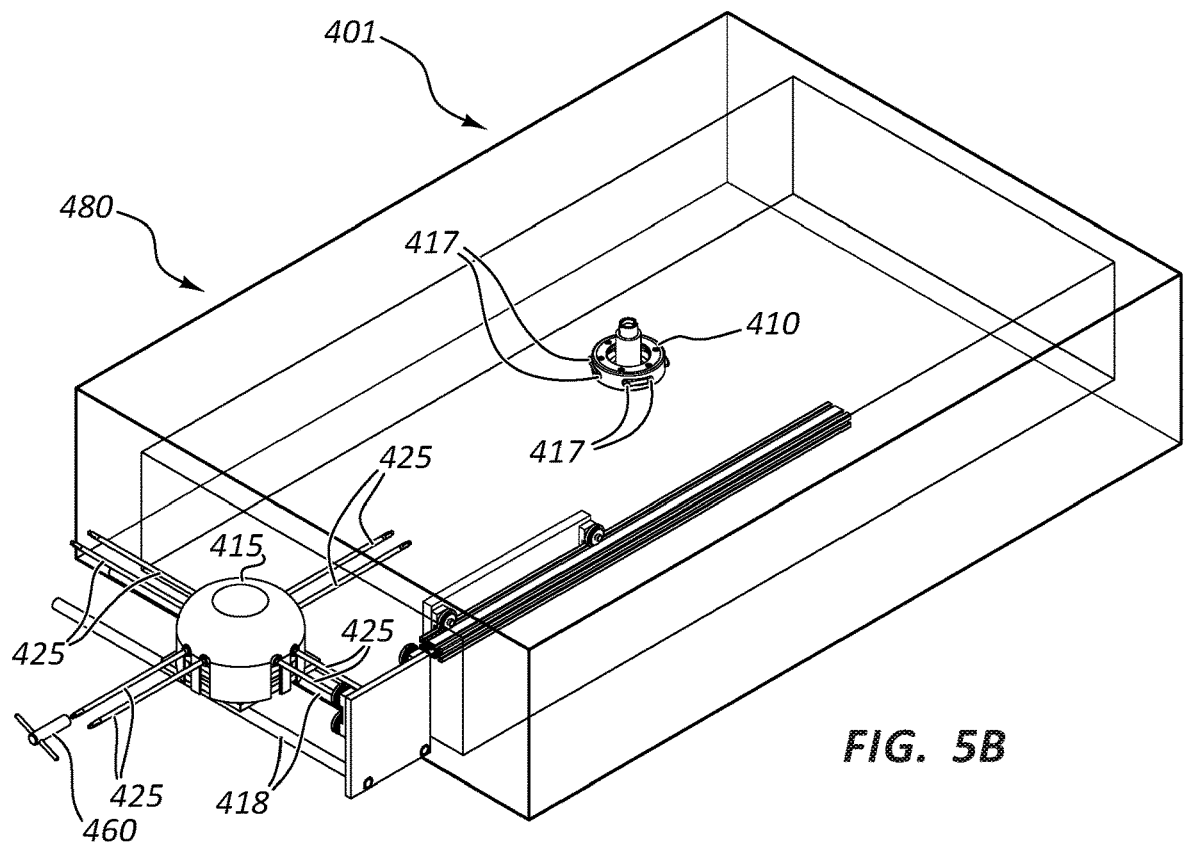
FIG. 5B is a perspective view of the same embodiment where a hub of the rotational spinning apparatus has been rolled outside of a housing of the rotational spinning apparatus and also illustrating one embodiment of a tool configured to remove mandrels from the hub.

In the illustrated embodiment apparatus 401 further comprises a housing 480 configured to allow hub 415 to be rolled inside housing 480 during operation of apparatus 401 and configured to allow hub 415 to be rolled outside housing 480 when apparatus 401 is not in operation. Rolling hub 415 outside of housing 480 may make it easier to remove mandrels 425 from hub 415. In the illustrated embodiment, spinneret 410 is mounted and located in an upper portion of housing 480 such that spinneret 410 is located above hub 415 when hub 415 is rolled inside housing 480. FIG. 5A illustrates hub 415 rolled inside housing 480. FIG. 5B illustrates hub 415 rolled outside housing 480. Housing 480 is illustrated as supporting hub 415 via support rods 418. It should be understood any support structures compatible with the functions of hub 415 may be used.

Housing 480 may further comprise a retractable cover configured for insertion between spinneret 410 and hub 415. The retractable cover would be inserted between spinneret 410 and hub 415 during startup and shutdown of apparatus 401. While the retractable cover is in place spinneret 410, hub 415, and/or each mandrel 425 may be either brought up to operational speed or shutdown. The retractable cover would then be removed when spinneret 410, hub 415, and mandrels 425 are at operational speed. In this way, fibers produced by spinneret 410 at less than optimal speeds would not be deposited on mandrels 425.

Figure 6A:
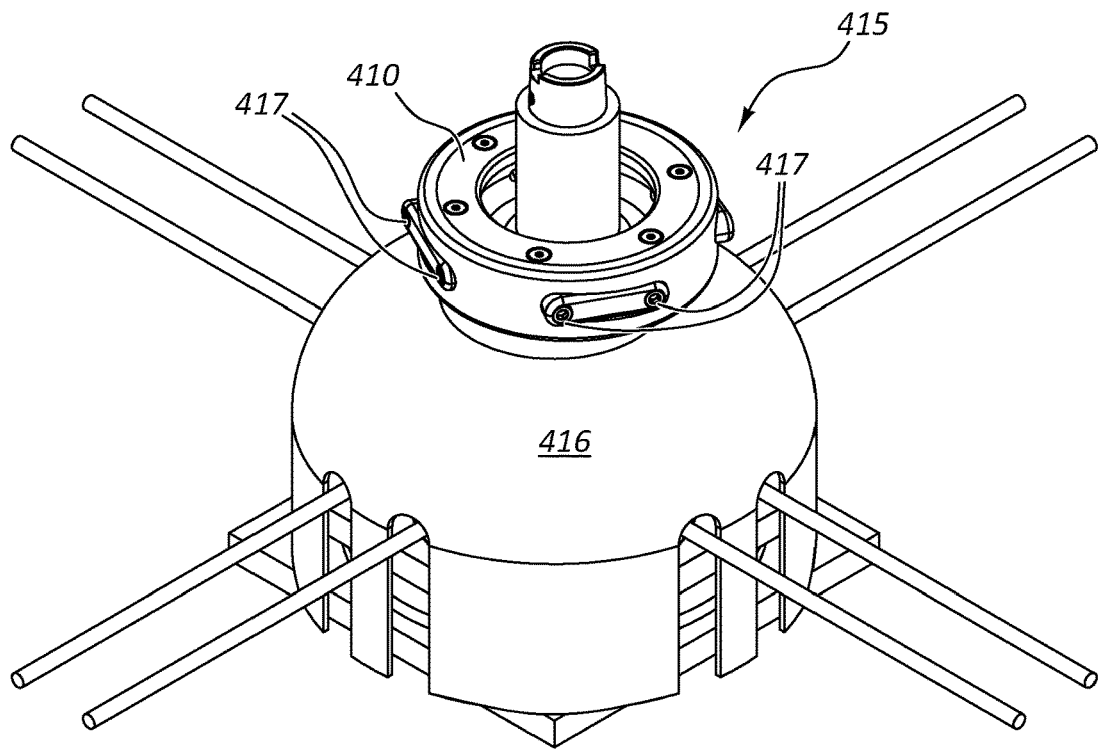
FIG. 6A is a perspective view of the hub of FIGS. 5A and 5B.
Figure 6B:
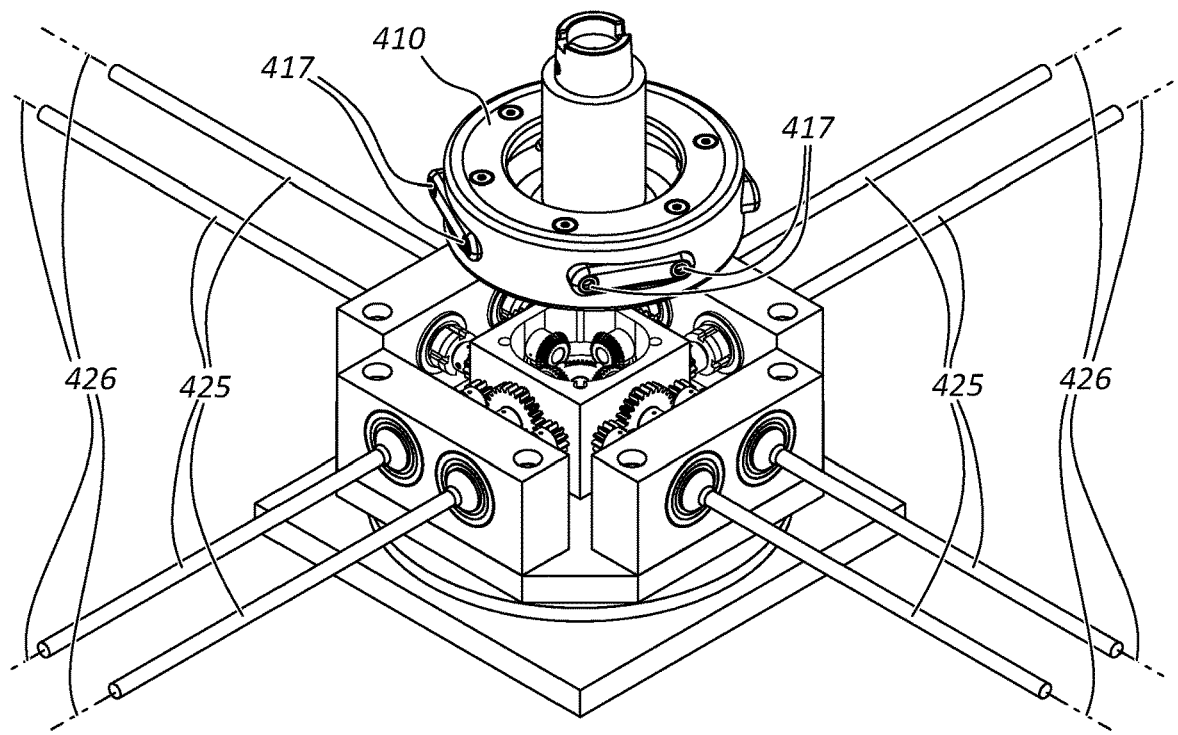
FIG. 6B is the same perspective view as in FIG. 6A, but without a shell of the hub.

FIG. 6A illustrates hub 415 with a shell 416 in place and with spinneret 410 oriented above hub 415. It should be understood that none of the supporting structures for hub 415 or spinneret 410 are shown in this Figure. FIG. 6B illustrates hub 415 without shell 416. Shell 416 may be configured in any manner compatible with keeping fibers out of actuating components of hub 415. In apparatus 401, mandrels 425 extend horizontally outward from hub 415 so that each mandrel's 425 own axis of rotation 426 lies in a plane that is perpendicular to the line of first axis of rotation 406. In apparatus 401, some of the mandrel's own axes of rotation 426 are the same as each other, but different from first axis of rotation 406. In apparatus 401, each mandrel 425 has a corresponding opposite mandrel 425 that extends outwardly from hub 415 in the opposite direction. In apparatus 401, each mandrel 425 and its corresponding opposite mandrel 425 each have the same own axis of rotation 426.

In the illustrated embodiment, the gears that actuate mandrels 425 are synchronized together so that each mandrel 425 turns at the same speed. Hub 415 may be configured such that different mandrels 425 turn at different speeds. Hub 415 may include actuators configured to rotate mandrels 425 and actuators configured to rotate hub 415. For example, a stationary actuator may be operably coupled underneath hub 415 and configured to rotate hub 415. Additionally, a rotatable actuator may be coupled to hub 415 and configured to rotate with hub 415 and rotate mandrels 425 at the same time.

Figure 7:
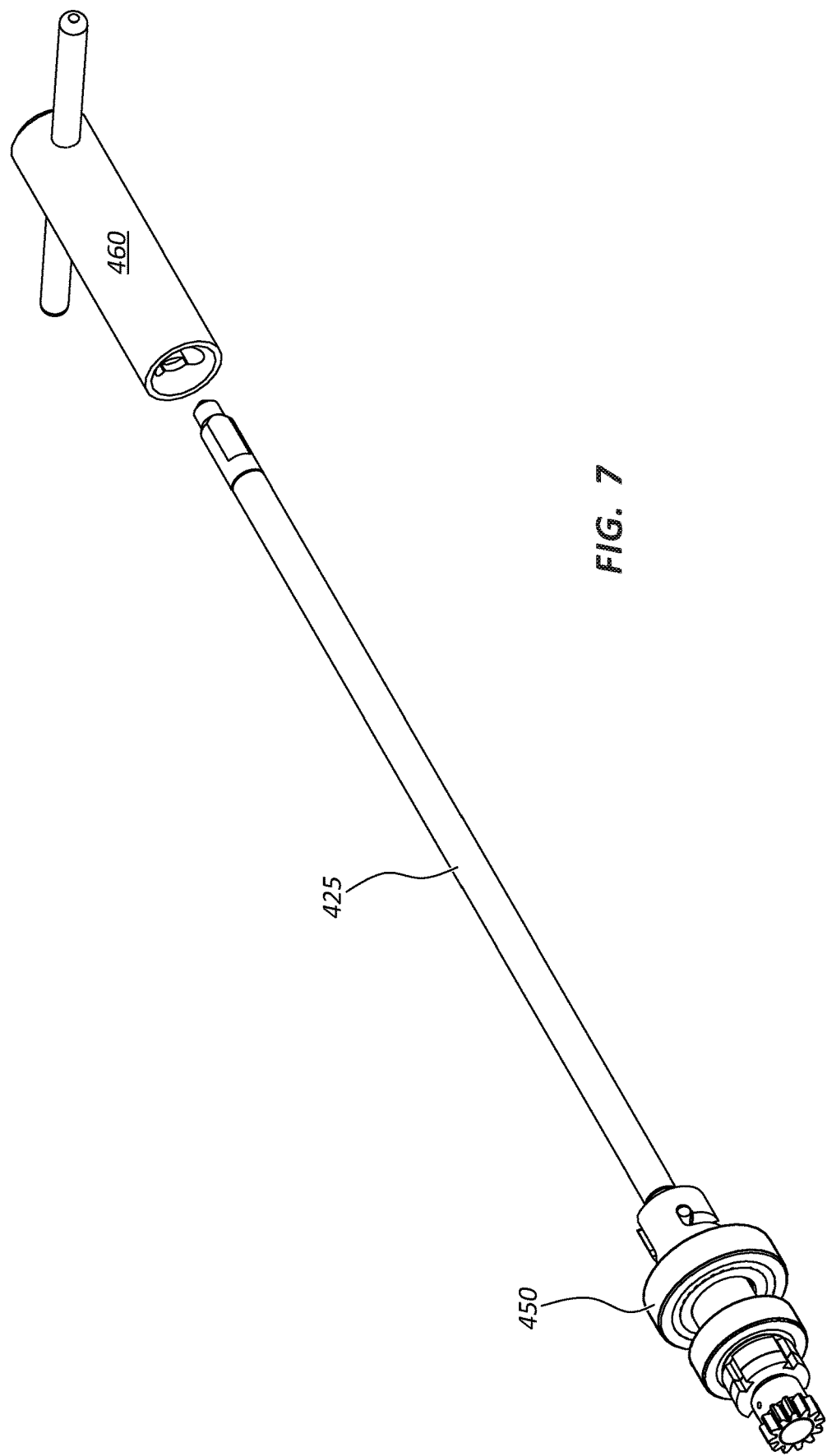
FIG. 7 further illustrates the tool of FIG. 6B and the mandrel of FIG. 6B removed from the hub.

FIG. 7 illustrates mandrel 425 separated from hub 415. In FIG. 7, mandrel 425 is illustrated with a cog 450 attached to the proximal end of mandrel 425. It should be understood that cog 450 may be retained in hub 415 and mandrel 425 removed from cog 450. FIGS. 5B and 7 illustrate a tool 460. Tool 460 is not a part of apparatus 401, but may be used with apparatus 401 to remove mandrels 425 from hub 415. The distal ends of mandrels 425 may be configured to mate with tool 460. Tool 460 may be configured such that an individual using tool 460 may able to remove mandrels 425 from hub 415 using only tool 460. This may prevent damage to unsintered fibers deposited on mandrels 425.

Mandrels 425 may be configured for removal from hub 415 using a quick connect coupling. As used herein, a "quick connect coupling" is any device, connector or attachment mechanism that allows removal of mandrels 425 in less than 10 seconds. For example, FIG. 7 illustrates one embodiment of a quick connect coupling. Cog 450 includes a socket configured to receive the proximal end of a mandrel 425. The socket of cog 450 includes a J-shaped slot in the sidewall of the socket. Mandrel 425, in this illustrated embodiment, includes a peg protruding from the side of the proximal end of the mandrel 425. The peg is sized and configured to slide within the J-shaped slot of the sidewall of the socket. During insertion of a mandrel 425 into the socket of cog 450, the peg is lined up with the long side of the J-shaped slot. Next, mandrel 425 is pushed into the socket, rotated, and then slightly pulled back until the peg has completely travelled the length of the J-shaped slot. Mandrel 425 is now ready for rotation by hub 415. Removal of a mandrel 425 from the socket of a cog 450 follows a reverse process. Likewise, for removal of cog 450, such as for cleaning or maintenance, with the peg of a mandrel 425 fully engaged with the J-shaped slot, mandrel 425 can be twisted and pulled for disengagement of cog 450 from hub 415 and pushed and twisted for reengagement of cog 450.

Regarding mandrels 125, 225, 325, and 425, one benefit of rotating the plurality of mandrels around the same first axis of rotation as the spinneret is that rotational speed may be optimized. For example, the optimal speed for producing a fiber, such as a PTFE fiber, of a particular diameter and length may be about 7,500 RPM. The optimal speed at which the fibers contact the mandrels may be about 6,500 RPM. Under that scenario, the disk or hub may be rotated at about 1,000 RPM in the same direction as the rotation of the spinneret so that the net speed difference between the rotating fibers and the mandrels around the first axis of rotation is about 6,500 RPM. Of course, the orientation of each mandrel's own axis of rotation, and rotational direction and speed of rotation of the mandrels around each mandrel's own axis of rotation may also be optimized.

Regarding mandrels 125, 225, 325, and 425, the spinning motion of each mandrel may tend to deposit the fibers around the entire surface of the mandrel. Thus, as the fibers are deposited on each mandrel, a seamless tube of fiber material may form on each mandrel. The density of the fibers, the thickness of the tube of material, and other characteristics may be controlled by such variables as the distance from the spinneret to the mandrels, the rotational speed and direction of the spinneret, the rotational speed and direction of the disk around the first axis of rotation, the rotational speed and direction of each of the mandrels around its own axis of rotation, the number and orientation of the mandrels, the characteristics of the flowable material being spun, and so forth. In some instances, the rotational spun material formed on a mandrel may thus comprise a tubular membrane having no seam and substantially isotropic properties.

Furthermore, controlling the rotational speed of the disk and the mandrels may influence both the density of the material formed on the mandrels and the general alignment of fibers in the material. For instance, in some embodiments utilizing vertical mandrels (i.e., a mandrel's own axis of rotation is parallel to the first axis of rotation), the faster the mandrel is spinning the more the fibers may tend to be deposited in-line with other fibers. Further, the relative density of the fibers, for example, as measured by percent porosity, may be controlled in part by the rotational speed of the mandrels.

Likewise, the orientation of the mandrels may influence the general alignment of fibers in the material. For example, when the mandrels are oriented parallel to the upper surface of the disk with each mandrel's own axis of rotation perpendicular to the first axis of rotation, such as illustrated in FIGS. 1A, 1B, 2, 3A, 3C, and 4, then fibers may cross each other at various and random points on the mandrels. This may have the benefit of the resulting tubular structure having isotropic properties, meaning the tubular structure has the same properties in all directions.

The distance between the spinneret and the mandrels may impact the diameter of the fibers. In some embodiments, the longer the fibers are drawn out before contacting the mandrels, the smaller the resulting fiber diameters. Similarly, smaller distances may be configured to produce larger diameter fibers. Thus, the spinneret to mandrel distance may be varied to achieve either microfibers or nanofibers.

Additional variables that may be controlled to affect the properties of a rotational spun tubular structure include the viscosity of the solution, dispersion, or other flowable material; the temperature of the spinneret; introduced air currents; and the thickness of the tubular structure. In the case of fibers spun from molten material, the melt flow index (MFI) of the material may also impact the nature of the spun tubular structure. In some embodiments, materials with an MFI of from about 1 g/10 min to about 5,000 g/10 min, including from about 200 g/10 min to about 1,500 g/10 min and from about 10 g/10 min to about 30 g/10 min, will tend to form fibers when spun.

As discussed previously, in some embodiments it may be desirable to sinter the fibers after they are deposited on the mandrels. Whether sintering is desirable may depend on the particular flowable material used to make the fibers. For example, sintering may be applicable to PTFE fibers, including PTFE fibers spun from a dispersion. The sintering process may set or bond the structure of the fibers and remove any remaining water or other dispersion medium or solvent.

In some embodiments, the fibers may be treated at a first temperature to remove solvents and a second temperature to sinter the fibers. For example, a PTFE tubular structure spun from an aqueous dispersion may be first treated at a temperature below the sintering temperature of PTFE in order to remove any remaining water. For example, the tubular structure may be heated to about 200 degrees C. to remove any remaining water in the tubular structure. Further, other materials such as solvents or fiberizing agents may be evaporated or otherwise driven off at this stage. In some embodiments—as further detailed below—a PTFE dispersion may be mixed with polyethylene oxide (PEO) prior to rotational spinning of the tubular structure. As also discussed in the examples below, concentrations of PEO to 60 wt % PTFE dispersion from about 0.04 g/ml to about 0.12 g/ml, including from about 0.06 g/ml to about 0.08 g/ml, may be used in some embodiments. In some instances, very high or very low concentrations of PEO may lead to shrinkage during sintering or sputtering during rotational spinning of the material.

Treating the spun tubular structure at temperatures such as 200 degrees C. may force off remaining PEO as well as water. In some embodiments the PTFE tubular structure may then be sintered at about 385 degrees C. In other embodiments, PTFE sintering may be completed at temperatures from about 360 degrees C. to about 400 degrees C., and/or at temperatures in excess of the crystalline melt point of the PTFE (about 342 degrees C.). In other instances the tubular structure may only be heated to the sintering temperature, removing the remaining water and/or PEO while simultaneously sintering the PTFE. Additionally or alternatively, in some embodiments solvents or other materials may be removed by rinsing the tubular structure.

Sintering may set the structure of the tubular structure even if the temperature at which the material is sintered is not sufficient to cause cross linking of the polymer chains. PTFE sintering may create solid, void-free PTFE fibers.

Processes such as the exemplary process described above may be utilized to create structures comprised of small-diameter fibers, including nanofibers. The fiber tubular structure may then be incorporated into a medical appliance configured for implantation in the human body. Some such structures, including nanofiber structures, may be configured to permit tissue ingrowth and/or endothelial growth or attachment on the tubular structure. For example, the tubular structure may be configured with openings within the fibers or similar structures configured to permit interaction with tissue and/or cells. As further detailed below, the percent porosity of a fiber tubular structure, the thickness of the tubular structure, and the diameter of the fibers comprising the tubular structure may each be configured to create a fiber tubular structure with desired properties, including a tubular structure that tends to permit or resist tissue ingrowth and/or endothelial growth or attachment.

In other embodiments a rotational spun tubular structure may be configured to resist tissue ingrowth into or through the tubular structure. In such embodiments, the tubular structure may be configured with very small pores, or effectively no pores at all, thus preventing tissue ingrowth into or through the tubular structure. Certain medical appliances may be constructed partially of rotational spun materials configured to permit tissue ingrowth and/or endothelial growth or attachment and partially of rotational spun materials configured to resist tissue ingrowth and/or attachment. Characteristics of the rotational spun fiber tubular structure, such as porosity and average pore size, may be controlled during the rotational spinning process to create certain tubular structures which permit tissue ingrowth and/or endothelial growth or attachment and other tubular structures which resist or are impermeable to tissue ingrowth and/or attachment.

In some embodiments, a PTFE dispersion may be used to rotationally spin a tubular structure comprised of PTFE nanofibers. Furthermore, in some exemplary embodiments PEO may be added to the PTFE dispersion prior to rotational spinning of the material. The PEO may be added as a fiberizing agent, to aid in the formation of PTFE fibers within the dispersion or during the process of rotational spinning of the material. In some instances the PEO may more readily dissolve in the PTFE dispersion if the PEO is first mixed with water. In some examples this increased solubility may reduce the time needed to dissolve PEO in a PTFE dispersion from as long as multiple days to as little as 30 minutes. After the material is rotational spun onto a mandrel, the material may then be sintered as further described below. In some instances the sintering process will tend to set or harden the structure of the PTFE. Furthermore, as described above, sintering may also eliminate the water and PEO, resulting in a tubular structure of substantially pure PTFE. Additionally, as also described above, the tubular structure may first be heat treated at a temperature below the sintering temperature of the PTFE, in order to remove water and/or PEO from the tubular structure. In some embodiments this step may be completed at about 200 degrees C.

The water, PEO, and PTFE amounts may be controlled to optimize the viscosity, PEO/PTFE ratio, or other properties of the mixture. In some instances adding water to the PEO before mixing with the PTFE dispersion may aid in reducing the number of solid chunks in the mixture, lower the preparation time for the mixtures, and reduce the time needed for the combined mixture to solubilize.

A variety of materials may be rotational spun to form structures for use in medical appliances. Exemplary materials which may be rotational spun for use in implantable appliances include PTFE, fluorinated ethylene propylene (FEP), Dacron or Polyethylene terephthalate (PET), polyurethanes, polycarbonate polyurethanes, polypropylene, Pebax, polyethylene, biological polymers (such as collagen, fibrin, and elastin), and ceramics.

Furthermore, additives or active agents may be integrated with the rotational spun materials, including instances where the additives are directly rotational spun with other materials. Such additives may include radiopaque materials such as bismuth oxide, antimicrobial agents such as silver sulfadiazine, antiseptics such as chlorhexidine or silver and anticoagulants such as heparin. Organic additives or components may include fibrin and/or collagen. In some embodiments, a layer of drugs or other additives may be added to a rotational spun appliance during manufacture. Additionally, some appliances may be constructed with a combination of synthetic components, organic components, and/or active ingredients including drugs, including embodiments wherein an appliance is comprised of alternating layers of these materials. Moreover, in some embodiments a medical appliance may consist of layers of rotational spun materials configured to control the release of a drug or another active layer disposed between such layers. Active layers or ingredients such as drugs or other active agents may be configured to reduce or otherwise modify or influence the biological response of the body to the implantation of the medical appliance.

Additionally, in some embodiments the material supplied to the internal reservoir of the spinneret may be continuously supplied (for example by a feed line), including embodiments where the reservoir is pressurized or supplied by a pressurized source. Further, in some embodiments the material may be heated near or above its melting point prior to rotational spinning, including embodiments wherein the material is melted and not dispersed in a solvent. Thus, in some embodiments, rotational spinning molten material does not include the use of solvents; therefore there is no need to remove solvents from the tubular structure at a later step in the process. In some instances the material may be supplied to the reservoir as pellets which are heated and melted within the reservoir.

Additionally, in some embodiments rotational spun structures may be combined with electrospun structures, including embodiments where some layers of material are rotational spun and some electrospun, but both deposited on the same mandrel. Electrospinning, and its use in connection with medical appliances, is described in U.S. patent application Ser. No. 13/360,444, filed on Jan. 27, 2012 and titled "Electrospun PTFE Coated Stent and Method of Use," which is hereby incorporated by reference in its entirety.

In some embodiments, rotational spun tubular medical devices, such as stents or grafts, may comprise one or multiple bifurcations or branches. Thus, medical devices which comprise a single lumen which splits or bifurcates into two or more lumens are within the scope of this disclosure. Likewise, medical appliances comprising a main lumen with one or multiple branch lumens extending from the wall of the main lumen are within the scope of this disclosure. For example, a thoracic stent—configured for deployment within the aorta—may comprise a main lumen configured to be disposed in the aorta and branch lumens configured to extend into side branch vessels originating at the aorta. Similarly, in some embodiments such tubular medical devices may alternatively be configured with access holes in the main lumen configured to allow access (possibly for additional stent or grafts placement) and flow from the main vessel to any branch vessels extending therefrom.

In some embodiments, a branched medical appliance may be manufactured by first creating a branched mandrel similar in shape to the desired branched medical appliance. The entire mandrel may then be rotated around the axis of the main lumen portion and rotational spun fibers collected over the entire surface of the mandrel. Any unwanted fibers between branches and/or the main lumen may be wiped off. The entire mandrel, with or without the actuator and disk, may then be placed in an oven and sintered. The appliance may then be removed from the mandrel and placed on or within a frame structure, such as a stent frame. A dip or film coating (such as of FEP or PTFE) may then be applied over the construct to create an impervious outside layer and/or to further bond the frame to the spun portion of the appliance.

In some embodiments, a branched medical appliance may be manufactured by first creating a branched mandrel in which the branched portions are removable from the portion of the mandrel coinciding with the main lumen. The leg or branch portions of the mandrel may be splayed 180 degrees apart with a common axis of rotation. Thus, in some embodiments, the entire mandrel may form a T-shape. The entire mandrel may then be rotated around the axis of the leg portions and rotational spun fibers collected on the leg portions of the mandrel. The mandrel may then be oriented to rotate around the axis of the main lumen portion of the mandrel, and any unwanted fibers disposed while spinning on the bifurcated leg portions may be wiped off. The mandrel may then be rotated around the axis of the main lumen portion and fibers collected on the main lumen portion of the mandrel. The entire mandrel, with or without the actuators and disk, may then be placed in an oven and sintered. The mandrel portions associated with the bifurcated legs may then be removed from the leg or branch portions of the appliance, and the single lumen mandrel portion subsequently removed from the spun appliance. The appliance may then be placed on or within a frame structure, such as a stent frame. A dip or film coating (such as of FEP or PTFE) may then be applied over the construct to create an impervious outside layer and/or to further bond the frame to the spun portion of the appliance.

The methods and apparatus disclosed herein may control the thickness of a tubular structure and thereby the relative permeability of the structure. As more and more fibers are rotational spun onto a tubular structure, the tubular structure may both increase in thickness and decrease in permeability (due to successive layers of strands occluding the pores and openings of layers below).

Tubular structures produced in connection with the present disclosure may be described by three general parameters: percent porosity, wall thickness, and fiber diameter. Each of these parameters may impact the nature of the tubular structure, including the tendency of the tubular structure to permit tissue ingrowth and/or endothelial attachment or the tendency of the tubular structure to resist tissue ingrowth or endothelial attachment. Each of these parameters may be optimized with respect to each other to create a tubular structure having particular characteristics.

Percent porosity refers to the percent of open space to closed space (or space filled by fibers) in a fiber non-woven material. Thus, the more open the non-woven material is, the higher the percent porosity measurement. In some instances, percent porosity may be determined by first obtaining an image, such as using a scanning electron microscope, of a rotational spun material. The image may then be converted to a "binary image," or an image showing only black and white portions, for example. The binary image may then be analyzed and the percent porosity determined by comparing the relative numbers of each type of binary pixel. For example, an image may be converted to a black and white image wherein black portions represent gaps or holes in the rotational spun material while white portions represent the fibers of the non-woven material. Percent porosity may then be determined by dividing the number of black pixels by the number of total pixels in the image. In some instances, a code or script may be configured to make these analyses and calculations.

In some embodiments, percent porosities from about 30% to about 80% may be configured to permit tissue ingrowth into the layer and/or permit endothelial growth or attachment on the layer, including tubular structures of about 40% to about 60%, tubular structures of about 45% to about 50%, or tubular structures of about 50% porosity. Less open layers may be configured to resist such ingrowth and/or attachment. Because the fibers comprising the tubular structures are deposited in successive layers, the second parameter, wall thickness, may be related to porosity. In other words, the thicker the wall, the more layers of fibers and the less porous the wall may be. In some embodiments, a wall with a thickness from about 20 micrometers to about 100 micrometers may be configured for use in connection with the present disclosure, including walls from about 40 micrometers to about 80 micrometers. Finally, the third parameter, fiber diameter, may be a measurement of the average fiber diameter of a sample in some instances. In some embodiments fiber diameters from about 50 nanometers to about 3 micrometers may be used in connection with the present disclosure. Notwithstanding these or other specific ranges included herein, it is within the scope of this disclosure to configure a tubular structure with any combination of values for the given parameters.

In some embodiments the "average pore size" of the tubular structure may be used as an alternative or additional measurement of the properties of the tubular structure. The complex and random microstructure of a rotational spun tubular structure presents a challenge to the direct measurement of the average pore size. Average pore size can be indirectly determined by measuring the permeability of the tubular structure to fluids using known testing techniques and instruments. Once the permeability is determined, that measurement may be used to determine an "effective" pore size of the rotational spun tubular structure. As used herein, the "pore size" of a rotational spun tubular structure refers to the pore size of a membrane which corresponds to the permeability of the rotational spun tubular structure when measured using ASTM standard F316 for the permeability measurement. This standard is described in ASTM publication F316 "Standard Test Methods for Pore Size Characteristics of Membrane Filters by Bubble Point and Mean Flow Pore Test," which is incorporated herein by reference. In some instances this test can be used as a quality control after configuring a tubular structure based on the three parameters (percent porosity, wall thickness, and fiber diameter) discussed above.

In some applications it may be desirable to create a medical appliance which is substantially impermeable. Such a layer may decrease the incidence of lumen tissue surrounding the medical appliance growing into or attaching to the medical appliance. This may be desirable in applications where the medical appliance is used to treat stenosis or other occlusions; an impermeable outer layer may prevent tissue from growing into or through the material toward or into the lumen of the medical appliance and reblocking or restricting the body lumen. In some embodiments a substantially impermeable outer layer may be produced by using a rotational spun tubular structure with a percent porosity from about 0% to about 50%, including about 25%; a thickness from about 20 micrometers to about 100 micrometers, including from about 40 micrometers to about 80 micrometers; and fiber diameters from about 50 nanometers to about 3 micrometers.

Additionally, or alternatively, a substantially impermeable tubular structure may have an average pore size of about 0 microns to about 1.5 microns. In other embodiments, the impermeable layer may have an average pore size of less than about 0.5 micron. In yet other embodiments, the impermeable layer may have an average pore size of less than about 1 micron. In some embodiments, the impermeable layer may be a layer other than the outer layer, such as a tie layer, an intermediate layer, or an inner layer.

In one example, a medical appliance such as stent or graft may be covered with a rotational spun PTFE inner layer and a rotational spun PTFE outer layer. The outer layer may be configured to be substantially impermeable to tissue ingrowth and/or attachment. In other embodiments the impermeability of the stent or graft may be provided by a tie layer disposed between the outer layer and the inner layer. For example, a substantially impermeable layer may be formed of FEP which is applied, for example, as a film or dip coating between rotational spun layers of PTFE. Furthermore, FEP may be rotational spun with a small average pore size to create a substantially impermeable layer. In some embodiments both the outer layer and the tie layer may be configured to be substantially impermeable.

Dip coatings may be applied by dipping a portion of a layer or construct in a polymer dispersion. For example, a PTFE layer may be dip coated on a construct by adding 20 ml of water to 50 ml of a 60 wt % PTFE dispersion to thin the dispersion. A fiber tubular structure may then be dipped in the solution to coat the structure. The dip coat may then be sintered at 385 degrees C. for 15 minutes. Other concentrations of PTFE dispersions for dip coatings are also within the scope of this disclosure.

Further, an FEP layer may be dip coated on a construct by adding 20 ml of water to 50 ml of a 55 wt % dispersion to thin the dispersion. A fiber tubular structure may then be dipped in the solution to coat the tubular structure. The dip coat may then be cooked, for example, at 325 degrees C. for 15 minutes. Other concentrations of FEP dispersions for dip coatings are also within the scope of this disclosure. Additionally, polymer dispersions may be sprayed or otherwise applied onto a surface (such as a fiber tubular structure) to coat the surface. Such coatings may be heat treated after application.

In some embodiments, more or less water, for example from about 10 ml to about 50 ml, may be added to similar amounts and concentrations of the dip dispersions above to thin the dispersions. Additionally, substances other than, or in addition to, water may be used to thin a dispersion for dip coating. For example, a surfactant or a solvent may be used. In some such cases the surfactant or solvent may later be removed from the construct, including embodiments where it is allowed to evaporate when the coat is sintered or cooked. Alcohols, glycols, ethers, and so forth may be so utilized.

In some embodiments it may be desirable to create a medical appliance such as a stent or graft with an outer layer which is more porous. A porous outer layer may permit healing and the integration of the prosthesis into the body. For instance, tissue of the surrounding lumen may grow into the porous outer surface or attach to the outer surface layer. This tissue ingrowth may permit, modulate, and/or influence healing at the therapy site. In some embodiments a porous outer layer may be formed of rotational spun PTFE.

In certain embodiments a relatively porous inner layer may be desirable. This layer may or may not be used in conjunction with a substantially impermeable outer layer. A relatively porous inner layer may permit tissue ingrowth and/or endothelial attachment or growth on the inside surface of the stent or graft which may be desirable for any combination of the following: healing, biocompatibility, prevention of thrombosis, and/or reduction of turbulent blood flow within the stent or graft. In some embodiments the inner layer may be comprised of a tubular structure, such as a rotational spun PTFE tubular structure, having a percent porosity of about 40% to about 80%, including about 50%; a thickness of about 20 micrometers to about 100 micrometers, including from about 40 micrometers to about 80 micrometers; and fiber diameters from about 50 nanometers to about 3 micrometers.

Lumens within the circulatory system are generally lined with a single layer (monolayer) of endothelial cells. This lining of endothelial cells makes up the endothelium. The endothelium acts as an interface between blood flowing through the lumens of the circulatory system and the inner walls of the lumens. The endothelium, among other functions, reduces or prevents turbulent blood flow within the lumen. The endothelium plays a role in many aspects of vascular biology, including atherosclerosis, creating a selective barrier around the lumen, blood clotting, inflammation, angiogenesis, vasoconstriction, and vasodilation.

A therapeutic medical appliance which includes a covering of porous or semi-porous material may permit the formation of an endothelial layer onto the porous surface of the blood contacting side of the medical device. Formation of an endothelial layer on a surface, or endothelialization, may increase the biocompatibility of an implanted device. For example, a stent or graft which permits the formation of the endothelium on the inside diameter (blood contacting surface) of the stent or graft may further promote healing at the therapeutic region and/or have longer-term viability. For example, a stent or graft coated with endothelial cells may be more consistent with the surrounding body lumens, thereby resulting in less turbulent blood flow or a decreased risk of thrombosis, or the formation of blood clots. A stent or graft which permits the formation of an endothelial layer on the inside surface of the stent or graft may therefore be particularly biocompatible, resulting in less trauma at the point of application, fewer side effects, and/or longer-term device viability.

Medical appliances including a covering of porous or semi-porous material may be configured to inhibit or reduce inflammatory responses by the body toward the tissue contacting side of the medical appliance, for example. Mechanisms such as an inflammatory response by the body toward the medical appliance may stimulate, aggravate, or encourage negative outcomes, such as neointimal hyperplasia. For example, a device configured to permit tissue ingrowth and/or the growth or attachment of endothelial cells onto the blood contacting side of the device may reduce the likelihood of negative flow characteristics and blood clotting. Similarly, a device so configured may mitigate the body's inflammatory response toward the material on, for example, the tissue or non-blood contacting side of the device. By modulating the evoked inflammatory response, negative outcomes such as the presence of bioactive inflammatory macrophages and foreign body giant cells may be reduced. This may aid in minimizing the chemical chain of responses that may encourage fibrous capsule formation surrounding the device and events stimulating neointimal hyperplasia.

A relatively porous tubular structure may be comprised of a rotational spun tubular structure, such as PTFE, with an average pore size of about 1 micron to about 12 microns, such as from about 2 microns to about 8 microns, or from about 3 microns to about 5 microns, or alternatively from about 3.5 microns to about 4.5 microns.

In some embodiments a tie layer may be configured to promote bonding between the outer layer and the inner layer. In other embodiments the tie layer may further be configured to provide certain properties to the stent or graft as a whole, such as stiffness or tensile strength. The tie layer may thus be configured as a reinforcing layer. In some embodiments, expanded PTFE (ePTFE) may be configured as a reinforcing layer. ePTFE may be anisotropic, meaning having differing properties in differing directions. For example, ePTFE may tend to resist creep in the direction the ePTFE membrane was expanded. A reinforcing layer of ePTFE may be oriented to increase strength, resist creep, or impart other properties in a particular direction. ePTFE may be oriented such that the expanded direction is aligned with an axial direction of a medical device, with a transverse direction, with a radial direction, at any angle to any of these directions, and so forth. Similarly, multiple layers of ePTFE may be disposed to increase strength, resist creep, or impart other properties in multiple directions. The reinforcing layer may or may not be impermeable.

Additionally, in embodiments where both the inner layer and the outer layer are porous in nature, the tie layer may be configured to create an impermeable layer between the two porous layers. In such embodiments the stent or graft may permit tissue ingrowth, tissue attachment, and/or healing on both the inner and outer surfaces of the stent or graft while still preventing tissue outside of the stent or graft from growing into the lumen and occluding the lumen. Thus, tie layers may be configured to create a mid-layer portion of a construct, the tie-layer configured to inhibit tissue ingrowth into the layer or to be impervious to tissue migration into or through the layer, or to substantially inhibit tissue migration.

Furthermore, the tie layer may be configured to be impervious or substantially impervious to fluid migration across the tie layer. Specifically, constructions comprising one or more porous layers may allow fluid to cross the porous layer. In the case of a medical appliance configured to control blood flow, such as a graft, a porous layer may allow blood to leak across the layer or may allow certain smaller components of the blood to cross the layer while containing larger components, effectively filtering the blood. In some instances this filtration or ultrafiltration may allow components such as plasma to cross the barrier while containing red blood cells, leading to seroma. Thus, a fluid impermeable tie layer may be configured to contain fluid within a medical device also comprised of porous layers. In some devices, a tie layer may be both fluid impermeable and impervious to tissue ingrowth, or may be configured with either of these properties independent of the other. Constructs wherein any layer (other than or in addition to a tie layer) is configured to be fluid impermeable and/or impervious to tissue ingrowth are also within the scope of this disclosure. Thus, disclosure recited herein in connection with fluid impermeable and/or tissue impervious tie layers may be analogously applied to impermeable layers at various locations within a construct.

The tie layer (or any impermeable/impervious layer) may include any thermoplastic material and may or may not be rotational spun. In one embodiment, the tie layer may be ePTFE. In another it may be rotational spun PTFE. In other embodiments it may be FEP, including rotational spun FEP and FEP applied as a film or dip coating. Furthermore, the tie layer may include any of the following polymers or any other thermoplastic: dextran, alginates, chitosan, guar gum compounds, starch, polyvinylpyridine compounds, cellulosic compounds, cellulose ether, hydrolyzed polyacrylamides, polyacrylates, polycarboxylates, polyvinyl alcohol, polyethylene oxide, polyethylene glycol, polyethylene imine, polyvinylpyrrolidone, polyacrylic acid, poly(methacrylic acid), poly(itaconic acid), poly(2-hydroxyethyl acrylate), poly(2-(dimethylamino)ethyl methacrylate-co-acrylamide), poly(N-isopropylacrylamide), poly(2-acrylamido-2-methyl-1-propanesulfonic acid), poly (methoxyethylene), poly(vinyl alcohol), poly(vinyl alcohol) 12% acetyl, poly(2, 4-dimethyl-6-triazinylethylene), poly(3-morpholinylethylene), poly(N-1,2,4-triazolyethylene), poly (vinyl sulfoxide), poly(vinyl amine), poly(N-vinyl pyrrolidone-co-vinyl acetate), poly(g-glutamic acid), poly(Npropanoyliminoethylene), poly(4-amino-sulfo-aniline), poly [N-(p sulphophenyl)amino-3-hydroxymethyl-1,4-phenyleneimino-1,4-phenylene], isopropyl cellulose, hydroxyethyl, hydroxylpropyl cellulose, cellulose acetate, cellulose nitrate, alginic ammonium salts, i-carrageenan, N-[(3'-hydroxy-2',3'-dicarboxy) ethyl]chitosan, konjac glocomannan, pullulan, xanthan gum, poly(allyammonium chloride), poly(allyammonium phosphate), poly(diallydimethylammonium chloride), poly(benzyltrimethylammonium chloride), poly(dimethyldodecyl(2-acrylamidoethyly) ammonium bromide), poly(4-N-butylpyridiniumethylene iodine), poly(2-N-methylpridinium methylene iodine), poly(N methylpryidinium-2,5-diylethenylene), polyethylene glycol polymers and copolymers, cellulose ethyl ether, cellulose ethyl hydroxyethyl ether, cellulose methyl hydroxyethyl ether, poly(l-glycerol methacrylate), poly(2-ethyl-2-oxazoline), poly(2-hydroxyethyl methacrylate/methacrylic acid) 90:10, poly(2-hydroxypropyl methacrylate), poly(2-methacryloxyethyltrimethylammonium bromide), poly(2-vinyl-1-methylpyridinium bromide), poly(2-vinylpyridine N-oxide), poly(2-vinylpyridine), poly(3-chloro-2-hydroxypropyl 2-methacryloxyethyldimethylammonium chloride), poly(4-vinylpyridine N-oxide), poly(4-vinylpyridine), poly (acrylamide/2-methacryloxyethyltrimethylammonium bromide) 80:20, poly(acrylamide/acrylic acid), poly(allylamine hydrochloride), poly(butadiene/maleic acid), poly(diallyldimethylammonium chloride), poly(ethyl acrylate/acrylic acid), poly(ethylene glycol) bis(2-aminoethyl), poly (ethylene glycol) monomethyl ether, poly(ethylene glycol)bisphenol A diglycidyl ether adduct, poly(ethylene oxide-b-propylene oxide), poly(ethylene/acrylic acid) 92:8, poly(llysine hydrobromide), poly(l-lysine hydrobromide), poly (maleic acid), poly(n-butyl acrylate/2-methacryloxyethyltrimethylammonium bromide), poly(Niso-propylacrylamide), poly (N-vinylpyrrolidone/2-dimethylaminoethyl methacrylate), dimethyl sulfatequaternary, poly(N-vinylpyrrolidone/vinyl acetate), poly(oxyethylene) sorbitan monolaurate (Tween 20®), poly (styrenesulfonic acid), poly(vinyl alcohol), N-methyl-4(4'-formylstyryl)pyridinium, methosulfate acetal, poly(vinyl methyl ether), poly(vinylamine) hydrochloride, poly(vinylphosphonic acid), poly(vinylsulfonic acid) sodium salt, and polyaniline.

Regardless of the material, the tie layer may or may not be rotational spun. Further, in certain embodiments the stent or graft may include two or more tie layers. The tie layer may be formed in any manner known in the art and attached to the inner and outer layers in any manner known in the art. For example, the tie layer may comprise a sheet of material which is wrapped around the inner layer or a tube of material which is slipped over the inner layer which is then heat shrunk or otherwise bonded to the inner and outer layers. Further, in embodiments where the tie layer is rotational spun, it may be rotational spun directly onto the inner layer, the scaffolding, or both. In some instances the tie layer may be melted after the stent or graft is constructed to bond the tie layer to adjacent layers of the stent or graft covering.

Furthermore, tie layers may be configured to change the overall properties of the medical appliance. For example, in some instances a cover or construct comprised solely of rotational spun PTFE (of the desired pore size) may not have desired tensile or burst strength. A tie layer comprised of a relatively stronger material may be used to reinforce the PTFE inner layer, the PTFE outer layer, or both. For example, in some instances FEP layers may be used to increase the material strength of the cover. Again, as discussed above, the tie layer may also be configured as a portion of the construct configured to be impervious to tissue ingrowth or migration.

Further, one or more layers of rotational spun PTFE may be used in connection with a scaffolding structure. In other words, the disclosure above relating to covers, layers, tie layers, and related components is applicable to any type of scaffolding structure as well as to stents or grafts with no separate scaffolding structure at all.

In some embodiments, once the inner layer is sintered, the tube of material may be removed from the mandrel. The inner layer may be "peeled" from the mandrel to initially break any adherence of the inner layer to the mandrel. The inner layer may also be removed by pushing the covering with respect to the mandrel, causing the material to bunch as it is removed from the mandrel. In some embodiments, low-friction coatings may alternatively or additionally be applied to the mandrel before the inner layer is rotational spun. The inner layer may then be reapplied to the mandrel, by slipping the inner layer over the mandrel.

Once the inner layer is reapplied to the mandrel, a wire scaffolding can be formed over the mandrel and the inner layer. An outer layer of material may then be rotational spun onto the scaffolding and the inner layer. The entire construct may then be sintered. Additional layers may also be added through similar processes.

Many variations to the above-described process are within the scope of the present disclosure. For example, one or more layers may be applied by wrapping strips or mats of material around the mandrel and/or the other layers. Further, some of the layers may be applied by spray or dip coating the mandrel and/or the other layers. It is within the scope of this disclosure to vary the process above so long as at least one of the layers is rotational spun using a method and/or system disclosed herein.

In another example, a stent or graft may be comprised of an inner layer of rotational spun PTFE, a tie layer of FEP, and an outer layer of PTFE. The properties of each of these layers, including percent porosity, wall thickness, fiber diameter, and/or average pore size, may be controlled to form a covering layer that inhibits the growth of tissue into or through a particular layer or that permits endothelial growth or attachment on a particular layer.

In some such embodiments, the inner layer of PTFE may be spun on a mandrel, sintered, removed from the mandrel, replaced on the mandrel, and then a scaffolding structure applied around the inner layer. The FEP tie layer may then be applied by dipping, spraying, applying a film layer, electrospinning, rotational spinning, extrusion, or other processing.

In some embodiments, the FEP layer may be heated such that the FEP becomes soft, in some cases flowing into open spaces in adjacent PTFE layers. This may tie the FEP layer to adjacent PTFE layers. In some instances, heating the construct to about 325 degrees C. may allow the FEP to partially flow into openings in adjacent PTFE layers, without the FEP completely flowing through the PTFE layer.

In another particular example, an inner layer of PTFE may be rotational spun on a mandrel, sintered, removed, reapplied, and then a scaffolding structure applied around the inner layer. An FEP tie layer may then be applied as a film layer. In some instances this tie layer may be "tacked" into place, for example, by a soldering iron. A tube of PTFE (which may be formed separately by rotational spinning onto a mandrel and sintering) may then be disposed over the FEP film layer. The entire construct may then be pressured, for example, by applying a compression wrap. In some embodiments this wrap may comprise any suitable material, including a PTFE-based material. In other embodiments a Kapton film may be wrapped around the construct before the compression wrap, to prevent the construct from adhering to the compression wrap.

The compressed layers may then be heated above the melting temperature of the FEP tie layer, but below the sintering temperature of the PTFE. For example, the melt temperature of the FEP may be from about 264 degrees C. to about 380 degrees C., including about 325 degrees C. PTFE may be sintered at temperatures from about 360 degrees C. to about 400 degrees C. Thus, the entire construct may be heated to an appropriate temperature such as about 325 degrees C. In some embodiments the construct may be held at this temperature for about 15 to about 20 minutes. Heating the FEP layer to about 325 degrees C. may allow the FEP layer to remain substantially impervious to tissue ingrowth and/or attachment, creating a "barrier" layer within the construct, while still adhering the FEP to adjacent layers of PTFE. In other embodiments, heating the construct to higher temperatures, such as about 350 degrees C. or more, may be configured to allow the FEP to flow around the PTFE such that the entire construct has a higher degree of porosity and the FEP layer is not as impervious to ingrowth.

The joining of the FEP tie layer to the PTFE outer and inner cover layers may increase the strength of the finished covering. The construct may then be cooled and the compression wrap and the Kapton film discarded. The construct may then be removed from the mandrel.

A stent or graft formed by the exemplary process described above may be configured with desired characteristics of porosity and strength. In some instances the FEP material may coat the PTFE nanofibers but still allow for sufficient porosity to permit tissue ingrowth and/or endothelial attachment or growth. The degree to which the FEP coats the PTFE may be controlled by the temperature and time of processing. The lower the temperature and/or the shorter the time the construct is held at temperature, the less the FEP may flow. In some instances a tie layer of FEP which is impervious to tissue ingrowth into or through the layer may be formed by heating the construction only to about 270 degrees C.

A stent or graft may include a cuff at one or both ends of the stent or graft. The cuff may comprise an additional covering layer on the outside diameter of the stent or graft, disposed adjacent to the end of the stent or graft. The cuff may be configured to promote tissue ingrowth, attachment, and/or incorporation into the cuff. For example, the cuff may be more porous than an outer layer of the covering of the stent or graft. Factors such as porosity, type of covering or coating, type of material, use of organic material, and/or use or composite materials formed of synthetic material and organic material may be used to create a cuff configured for tissue ingrowth. Again, the cuff may be configured to promote tissue ingrowth and/or the growth or attachment of endothelial cells at one or both ends of the stent or graft. When implanted in the body, the cuffs may tend to "anchor" the ends of the stent or graft with respect to the vessel walls, reducing the relative movement of the stent or graft ends with respect to the vessel walls. Such a reduction in movement may lessen irritation of the vessel by the stent or graft ends, minimizing complications such as stenosis. Cuffs may be configured for use in central venous occlusion-type applications in some instances. Furthermore, a band of porous material analogous to a stent or graft cuff may be coupled to any medical appliance to anchor a portion of such a device.

In some embodiments, the outer layer of the covering of the stent or graft may be relatively non-porous to inhibit tissue ingrowth into or through the outer layer, but the cuff, disposed about the outer layer, may provide a section near each end at which some tissue ingrowth, attachment, and/or incorporation may occur.

The cuff may be comprised of a rotational spun material, such as PTFE, and may be bonded to the outer covering layer through any method, including methods of multilayer device construction described herein. For example, a layer of FEP may be disposed between the outer covering layer and the cuff and heated to bond the layers. In other embodiments the cuff may comprise a collagen layer which is coupled to the stent or graft. Further, a co-rotational spun collagen and PTFE cuff may be utilized.

In some embodiments, the medical appliances, including stents and grafts, may comprise a frame structure provided in connection with one or more coverings or coatings. It will be appreciated that, though particular structures, coverings, and coatings are described herein, any feature of the frames or coverings and/or coatings described herein may be combined with any other disclosed feature without departing from the scope of the current disclosure.

Frames for use in connection with medical appliances may be fabricated or formed into particular geometries through a variety of means. For example, a frame may be cut from a single tube of material, including embodiments wherein the frame is first laser cut, then expanded. In other embodiments, the frame may be molded, including embodiments wherein the frame is molded from a polymeric material. In still other embodiments, powder metallurgical processes, such as powdered compression molding or direct metal laser sintering, may be used.

The frame may consist of a single continuous wire. The wire may be shaped in a wave-type configuration. The frame may further be coupled to a covering layer. Additionally, in some embodiments, any covering as disclosed herein may be applied to any type of frame, for example, laser cut frames, polymeric frames, wire frames, and so forth.

The frame may be designed such that the midsection is "harder" than the ends. The "hardness" of the frame refers to the relative strength of the structure (e.g., its compressibility). A harder portion of the frame will have greater strength (i.e., exert a greater radial outward force) than a softer portion. In one embodiment, the midsection is harder than the proximal and distal end sections which are relatively softer. Further, a frame may be configured to be flexible to facilitate the ability of the device to conform to the native anatomy at which the device is configured for use. Similarly, covered devices may be configured with covers which conform to the native anatomy at a therapy site.

Additionally, the frame may be configured to allow the entire device to be crimped into a relatively low-profile configuration for delivery. For example, devices of a certain diameter or constrained profile are more feasible for delivery at certain vascular or other access points than others. For example, in many instances a device configured for insertion via the radial artery may be relatively smaller than devices configured for insertion via the generally larger femoral artery. A frame may be configured to be crimped into a particular profile to enable potential access at various or desired access points. Similarly, devices having no frame may be configured to be disposed in a particular profile to facilitate access and delivery. Once a device is positioned within the body it may be expanded or deployed in a number of ways, including use of self-expanding materials and configurations. Additionally, some configurations may be designed for expansion by a secondary device, such as a balloon.

The overall frame design may be configured to optimize desired radial force, crush profile, and strain profile. Methods of designing frames are known in the art and are also disclosed in U.S. patent application Ser. No. 13/742,025, filed Jan. 15, 2013, the contents of which are incorporated herein in their entirety.

Furthermore, in some embodiments the frame may be configured with radiopaque markers at one or more points along the frame. Such markers may be crimped to the frame. In other embodiments a radiopaque ribbon, for example a gold ribbon, may be threaded or applied to the frame. In some embodiments these markers may be located at or adjacent to one or both ends of the frame. Any radiopaque material may be used, for example gold or tantalum. Radiopaque elements may be configured to facilitate the delivery and placement of a device and/or to facilitate viewing of the device under fluoroscopy.

In some embodiments, a stent, graft, or other tubular device may comprise a tapered segment along the length of the device. A taper may be configured to reduce the velocity of fluid flow within the device as the fluid transitions from a smaller diameter portion of the device to a larger diameter portion of the device. Reducing the fluid velocity may be configured to promote laminar flow, including instances wherein a tubular member is tapered to promote laminar flow at the downstream end of the device.

Use of rotational spun coatings may facilitate application of a covering of uniform thickness along a tapered stent or graft. For example, in some embodiments, rotational spun coatings may be configured to evenly coat devices comprised of various geometries. A rotational spun coating may deposit a substantially even coating along various geometries such as tapers, shoulders, and so forth.

While specific embodiments of stents, grafts, and other medical appliances have been illustrated and described, it is to be understood that the disclosure provided is not limited to the precise configuration and components disclosed. Various modifications, changes, and variations apparent to those of skill in the art having the benefit of this disclosure may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A method of making a rotational spun appliance, the method comprising:
   rotating a spinneret around a first axis of rotation to produce spinning fibers;
   rotating a plurality of mandrels, each mandrel rotating about its own axis of rotation, wherein each mandrel's axis of rotation is not the same as the first axis of rotation; and
   contacting the spinning fibers with the rotating mandrels, such that fibers are deposited on the mandrels;
   wherein each mandrel's own axis of rotation is perpendicular to the first axis of rotation.

2. The method of claim 1, wherein the plurality of mandrels are collectively and simultaneously rotating around the first axis of rotation.

3. The method of claim 1, wherein the rotation of each mandrel around its own axis of rotation results in the surface of the mandrel turning in the same direction as the spinning fibers are spinning.

4. The method of claim 1, wherein the rotation of each mandrel around its own axis of rotation results in the surface of the mandrel turning in an opposite direction as the spinning fibers are spinning.

5. The method of claim 1, wherein the fibers are microfibers or nanofibers.

6. The method of claim 1, wherein the fibers are polymer fibers.

7. The method of claim 1, further comprising placing fiber-wrapped mandrels in a sintering oven and sintering the fiber-wrapped mandrels.

8. The method of claim 1, wherein the rotational spun appliance is a stent, stent graft, or graft.

9. A method of manufacturing a component of a medical appliance, the method comprising:
   rotating a plurality of collection members to collect fibers ejected from a spinneret; and
   rotating the spinneret about a first axis of rotation to produce the fibers;
   wherein an axis of rotation of each collection member is perpendicular to the first axis of rotation.

10. The method of claim 9, wherein the collection members comprise mandrels.

11. The method of claim 10, wherein the mandrels are cylindrical.

* * * * *